(12) United States Patent
Fukami et al.

(10) Patent No.: US 7,304,072 B2
(45) Date of Patent: *Dec. 4, 2007

(54) SPIRO COMPOUNDS

(75) Inventors: Takehiro Fukami, Tsukuba (JP); Akio Kanatani, Tsukuba (JP); Akane Ishihara, Tsukuba (JP); Yasuyuki Ishii, Tsukuba (JP); Toshiyuki Takahashi, Tsukuba (JP); Yuji Haga, Tsukuba (JP); Toshihiro Sakamoto, Tsukuba (JP); Takahiro Itoh, Okazaki (JP); Masato Chiba, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 502 days.

This patent is subject to a terminal disclaimer.

(21) Appl. No.: 10/922,869

(22) Filed: Aug. 23, 2004

(65) Prior Publication Data

US 2005/0032820 A1 Feb. 10, 2005

Related U.S. Application Data

(63) Continuation-in-part of application No. PCT/JP03/02611, filed on Mar. 5, 2003, which is a continuation-in-part of application No. 10/092,549, filed on Mar. 8, 2002.

(51) Int. Cl.
*A61K 31/4355* (2006.01)
*C07D 491/048* (2006.01)

(52) U.S. Cl. ......................... 514/278; 546/15; 546/116; 546/167; 544/182; 544/331; 544/332; 544/336; 548/311.4; 548/364.4; 549/265; 514/275; 514/397

(58) Field of Classification Search ................. 514/278, 514/275, 397; 546/17, 15, 116, 167; 544/331, 544/332, 336, 182; 548/311.4, 364.4; 549/265
See application file for complete search history.

(56) References Cited

U.S. PATENT DOCUMENTS

| | | | |
|---|---|---|---|
| 6,326,375 B1 | 12/2001 | Fukami et al. | 514/278 |
| 6,335,345 B1 | 1/2002 | Fukami et al. | 514/275 |
| 6,388,077 B1 | 5/2002 | Fukami et al. | 546/15 |
| 6,462,053 B1 | 10/2002 | Fukami et al. | 514/278 |
| 6,649,624 B2 | 11/2003 | Fukami et al. | 514/278 |
| 6,723,847 B2 | 4/2004 | Fukami et al. | 544/331 |
| 6,803,372 B2 * | 10/2004 | Fukami et al. | 514/275 |
| 6,924,291 B2 * | 8/2005 | Song et al. | 514/278 |
| 2002/0151456 A1 | 10/2002 | Song et al. | 512/10 |

FOREIGN PATENT DOCUMENTS

| | | |
|---|---|---|
| EP | 0 615 977 | 9/1994 |
| WO | 99/27965 | 6/1999 |
| WO | 99/29696 | 6/1999 |
| WO | 00/27845 | 5/2000 |
| WO | 03/010175 | 2/2003 |

* cited by examiner

*Primary Examiner*—Charanjit S. Aulakh
(74) *Attorney, Agent, or Firm*—Wenderoth, Lind & Ponack, L.L.P.

(57) ABSTRACT

Compounds represented by the general formula (I)

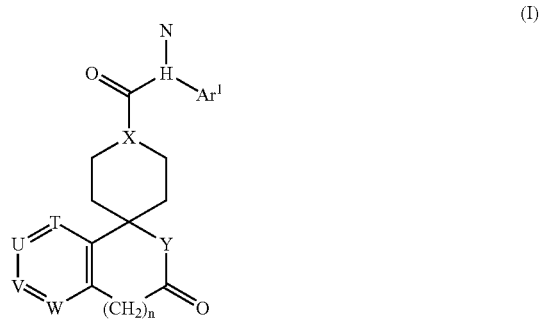

wherein $Ar^1$ represents an aryl or heteroaryl which may be substituted; n represents 0 or 1; T, U, V and W each independently represent a nitrogen atom or a methine group which may have a substituent selected from the group consisting of halogen, lower alkyl, hydroxy and lower alkoxy, wherein at least two of which represent said methine group; X represents methine, hydroxy substituted methine or nitrogen atom; Y represents an imino which may be substituted with lower alkyl, or oxygen; and a salt, ester or N-oxide derivative thereof. The compounds exhibit NPY antagonistic activities and are useful as agents for the treatment of various diseases related to NPY, for example, cardiovascular disorders, central nervous system disorders, metabolic diseases, sexual and reproductive dysfunctions, gastro-intestinal disorders, respiratory disorders, inflammation or glaucoma, and the like.

14 Claims, No Drawings

SPIRO COMPOUNDS

This application is a continuation-in-part of International Application No. PCT/JP03/02611 filed Mar. 5, 2003 and U.S. application Ser. No. 10/092,549 filed Mar. 8, 2002.

TECHNICAL FIELD

The present invention is useful in medical fields. In more detail, novel spiro compounds of this invention are useful as neuropeptide Y receptor antagonists and as agents for the treatment of various kinds of cardiovascular disorders, central nervous system disorders, metabolic diseases, and the like.

BACKGROUND ART

Neuropeptide Y (hereinafter referred to as NPY), a peptide consisting of 36 amino acids, was first isolated from porcine brain by Tatemoto et al. in 1982 [Nature, 296: 659 (1982)]. NPY is widely distributed in central nervous system and peripheral nervous system and plays various roles as one of the most abundant peptide in the nervous system. That is, NPY acts as an orexigenic substance in the central nervous system and markedly promotes fat accumulation via the mediation of the secretion of various hormones or the action of the nervous system. It is known that the continuous intracerebroventricular administration of NPY induces obesity and insulin resistance based on these actions (International Journal of Obesity, vol.19: 517 (1995); Endocrinology, vol.133: 1753(1993)). It is also known that NPY has central effects, such as depression, anxiety, schizophrenia, pain, dementia and the like (Drugs, vol. 52, 371(1996). Further, in the periphery, NPY coexists with norepinephrine in sympathetic ending and is involved in the tonicity of the sympathetic nervous system. It is known that peripheral administration of NPY causes vasoconstriction and enhances the activities of other vasoconstrictive substances such as norepinephrine (British Journal of Pharmacology, vol.95: 419 (1988)). It is also reported that NPY could participate in the development of cardiac hypertrophy as a result of the sympathic stimulation (Proceeding National Academic Science USA, Vol. 97, 1595(2000)).

On the other hand, it is reported that NPY is also involved in the secretory function of sexual hormones and growth hormone, sexual behavior and reproductive function, gastro-intestinal motility, bronchoconstriction, inflammation and alcohol preference (Life Science, vol. 55, 551(1994); The Journal of Allergy and Immunology, vol. 101, S345(1998); Nature, vol. 396, 366(1998)).

NPY has a variety of pharmacological effects which result from NPY binding to the NPY receptors. Other NPY related peptides, including peptide YY and pancreatic polypeptide also bind to the NPY receptors. It is known that these pharmacological effects are mediated by the action of, at least, five receptor subtypes with or without synergistic interactions. (Trends in Neuroscience, vol. 20, 294(1997)).

Y1: It is reported that the central effect mediated by NPY Y1 receptor includes the remarkable orexigenic effect (Endocrinology, vol. 137, 3177(1996); Endocrinology, vol. 141, 1011(2000)). Further, the Y1 receptor is reported to be involved in anxiety and pain (Nature, vol. 259, 528(1993); Brain Research, vol. 859, 361(2000)). In addition, the pressor effects mediated by the strong action of vasoconstriction in the periphery by NPY is also reported to be mediated by Y1 (FEBS Letters, vol. 362, 192(1995); Nature Medicine, vol. 4, 722(1998)).

Y2: It is known that the inhibitory effect on the release of various neurotransmitters in the sympathetic nerve endings is mediated by the NPY Y2 receptor (British Journal of Pharmacology, vol. 102, 41(1991); Synapse, vol. 2, 299 (1988)). In periphery, NPY causes constriction of blood vessel or vas deferens directly or via the control of release of various neurotransmitters (The Journal of Pharmacology and Experimental Therapeutics, vol. 261, 863(1992); British Journal of Pharmacology, vol. 100, 190(1990)). In addition, inhibition of lipolysis in adipose tissues is known (Endocrinology, vol. 131, 1970(1992)). Further, the inhibition of ion secretion in the gastrointestinal tract is reported (British Journal of Pharmacology, vol. 101 247(1990)).

On the other hand, the inhibitory effect on the central nervous system functions such as memory and anxiety is also reported (Brain Research, vol.503, 73(1989); Peptides, vol. 19, 359(1998)).

Y3: It is reported that NPY Y3 receptor is mainly located at brainstem and in the heart and is related to regulation of blood pressure and heart rate (The Journal of Pharmacology and Experimental Therapeutics, vol. 258, 633(1991); Peptides, vol. 11, 545(1990)). Further, it is known that the Y3 receptor is involved in the control of catecholamine secretion in adrenal gland ((The Journal of Pharmacology and Experimental Therapeutics, vol. 244, 468(1988); Life Science, vol. 50, PL7(1992)).

Y4: NPY Y4 receptor has high affinity for pancreatic polypeptide. The related pharmacological effects reported to be mediated by the Y4 receptor include the inhibition of pancreatic secretion and the gastro-intestinal motility (Gastroenterology, vol.85, 1411(1983)). Further, it is reported that NPY enhances the secretion of the sexual hormone in the central nervous system (Endocrinology, vol. 140, 5171 (1999)).

Y5: The effect mediated by NPY Y5 receptor includes feeding stimulation and accumulation of fat (Nature, vol. 382, 168(1996)); American Journal of Physiology, vol. 277, R1428(1999)). It is reported that the NPY Y5 receptor also mediates some CNS effects, such as seizure and epilepsy, or pain and the morphine withdrawal symptoms (Natural Medicine, vol. 3, 761(1997); Proceeding Academic Science USA, vol. 96, 13518(1999); The Journal of Pharmacology and Experimental Therapetics, vol. 284, 633(1998)). In the periphery, the Y5 receptor is reported to be involved in diuresis and hypoglicemic effect caused by NPY (British Journal of Pharmacology, vol. 120, 1335(1998); Endocrinology, vol. 139, 3018(1998)). NPY is also reported to enhance cardiac hypertrophy as a result of the sympathic accentuation (Proceeding National Academic Science USA, Vol. 97, 1595(2000)).

The effects of NPY occur by binding to the NPY receptors in the central or peripheral nervous system. Therefore, the action of NPY can be prevented by blocking the binding to NPY receptors. Substances antagonize NPY binding to NPY receptors may be useful for the prophylaxis or treatment of various diseases related to NPY, such as cardiovascular disorders (for example hypertension, nephropathy, heart disease, vasospasm), central nervous system disorders (for example bulimia, depression, anxiety, seizure, epilepsy, dementia, pain, alcoholism, drug withdrawal), metabolic diseases (for example obesity, diabetes, hormone abnormality), sexual and reproductive dysfunction, gastro-intestinal motility disorder, respiratory disorder, inflammation or glaucoma and the like (Trends in Pharmacological Sciences, 15: 153(1994); Life Science,. 55, 551(1994); Drugs, vol. 52, 371(1996); The Journal of Allergy and Immunology, vol. 101, S345(1998); Nature, vol. 396, 366(1998); The Journal of Pharmacology and Experimental Therapeutics, vol.284, 633(1998); Trends in Pharmacological Science, vol. 20, 104(1999); Proceeding National Academic Science USA, vol. 97, 1595(2000)).

Recently, according to the investigation of the present inventors, it has been found that some kind of NPY receptor antagonist is useful in the prophylaxis or treatment of hypercholesterolemia, hyperlipidemia and arteriosclerosis [International application publication WO99/27965].

DISCLOSURE OF INVENTION

The object of the present invention is to provide novel medicines which exhibit NPY antagonistic activities.

The present inventors have discovered that the compound of the general formula (I):

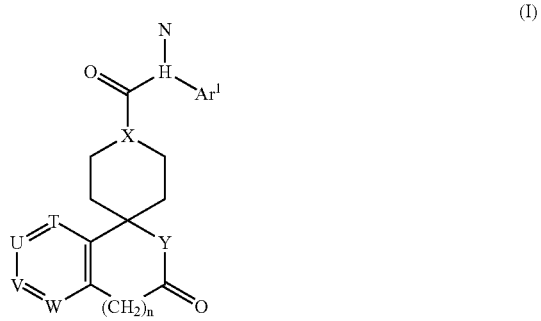

(I)

wherein $Ar^1$ represents aryl or heteroaryl which may be substituted, the substituent being selected from the group consisting of hydroxy, halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of $-Q-Ar^2$;

$Ar^2$ represents aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl;

n represents 0 or 1;

Q represents a single bond or carbonyl;

T, U, V and W represent independently nitrogen atom or methine group which may have a substituent selected from the group consisting of halogen, lower alkyl, hydroxy and lower alkoxy, where at least two of them represent the said methine group;

X represents methine, hydroxy substituted methine (namely methine substituted by hydroxy) or nitrogen atom;

Y represents imino which may be substituted with lower alkyl, or oxygen, and a salt, ester or N-oxide derivative thereof; particularly the compound of the formula (I) with the proviso that if the compound is not an N-oxide derivative, $Ar^1$ is a hydroxy substituted aryl or hetero-aryl group, or alternatively X is hydroxy substituted methine, as well as a salt, ester or N-oxide derivative thereof exhibit NPY antagonistic activities and is useful as a therapeutic agent for treatment of various diseases associated with NPY, thereby completing the present invention.

Compounds of the present invention (I) are useful as agents for the treatment of various diseases related to NPY, that is, for example cardiovascular disorders (for example hypertension, nephropathy, heart disease, vasospasm, arteriosclerosis), central nervous system disorders (for example bulimia, depression, anxiety, seizure, epilepsy, dementia, pain, alcoholism, drug withdrawal), metabolic diseases (for example obesity, diabetes, hormone abnormality, hypercholesterolemia, hyperlipidemia), sexual and reproductive dysfunction, gastro-intestinal disorder, respiratory disorder, inflammation, or glaucoma, and the like.

More particularly, compounds of this invention (I) is useful as agents for the treatment of bulimia, obesity, diabetes, and the like.

The present invention refers to compounds of the general formula (I), the salts, esters or N-oxide derivatives thereof, and the process for production and use. The compounds of the general formula (I), the salts, esters or N-oxide derivatives thereof, with the proviso that if the compound is not an N-oxide derivative, $Ar^1$ is a hydroxy substituted aryl or heteroaryl group, or alternatively X is hydroxy substituted methine, are preferable.

In another embodiment, the present invention is related to the intermediate for producing the compound represented by the general formula (I). Specifically, it is related to the compound represented by the general formula (VI-1):

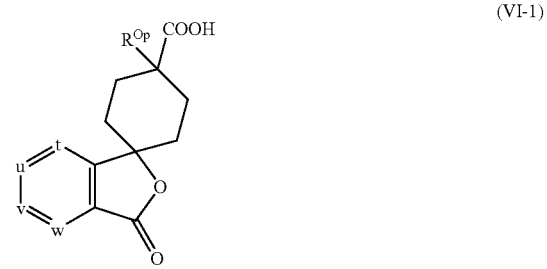

(VI-1)

wherein $R^{Op}$ represents hydrogen or optionally protected hydroxy; and t, u, v and w represent independently nitrogen atom or methine group which may have a substituent selected from the group consisting of halogen, lower alkyl, lower alkoxy and optionally protected hydroxy, where at least two of them represent the said methine group.

BEST MODE FOR CARRYING OUT THE INVENTION

The means of terms used in the present specification are defined and more detailed description of this invention is shown in the following.

"Halogen atom" refers to fluorine atom, chlorine atom, bromine atom and iodine atom.

"Lower alkyl" refers to a straight- or branched-chain alkyl group of C1 to C6, for example, methyl, ethyl, propyl, isopropyl, butyl, isobutyl, sec-butyl, tert-butyl, pentyl, isopentyl, hexyl, isohexyl, and the like.

"Halo(lower)alkyl" refers to the aforesaid lower alkyl substituted with 1 or more than 2, preferably 1 to 3 aforesaid halogen atoms identically or differently at the substitutable, arbitrary positions, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, and the like.

"Hydroxy(lower)alkyl" refers to the aforesaid lower alkyl substituted with 1 or more than 2, preferably 1 or 2 hydroxy groups at the substitutable, arbitrary positions, for example, hydroxymethyl, 2-hydroxyethyl, 1-hydroxy-1-methylethyl, 1,2-dihydroxyethyl, 3-hydroxypropyl, and the like.

"Cyclo(lower)alkyl" refers to a cycloalkyl group of C3 to C6, for example, cyclopropyl, cyclobutyl, cyclopentyl, cyclohexyl, and the like.

"Lower alkenyl" refers to a straight- or branched-chain alkenyl group of C2 to C6, for example, vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl, and the like.

"Lower alkoxy" refers to a straight- or branched-chain alkoxy group of C1 to C6, for example, methoxy, ethoxy, propoxy, isopropoxy, butoxy, sec-butoxy, isobutoxy, tert-butoxy, pentyloxy, isopentyloxy, hexyloxy, isohexyloxy, and the like.

"Halo(lower)alkoxy" refers to the aforesaid lower alkoxy substituted with 1 or more than 2, preferably 1 to 3 aforesaid halogen atoms identically or differently at the substitutable, arbitrary positions, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy, and the like.

"Lower alkylthio" refers to a straight- or branched-chain alkylthio group of C1 to C6, for example, methylthio, ethylthio, propylthio, isopropylthio, butylthio, sec-butylthio, isobutylthio, tert-butylthio, pentylthio, isopentylthio, hexylthio, isohexylthio, and the like.

"Lower alkanoyl" refers to an alkanoyl group containing the aforesaid lower alkyl, that is, an alkanoyl group of C2 to C7, for example acetyl, propionyl, butyryl, isobutyryl, valeryl, isovaleryl, pivaloyl, and the like.

"Lower alkoxycarbonyl" refers to an alkoxycarbonyl group containing the aforesaid lower alkoxy, that is, an alkoxycarbonyl group of C2 to C7, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, and the like.

"Lower alkylene optionally substituted with oxo" refers to a straight- or branched-chain alkylene group of C2 to C6 which may be substituted with 1 or more than 2, preferably 1 oxo group at a substitutable, arbitrary position, for example, ethylene, trimethylene, tetramethylene, pentamethylene, hexamethylene, 1-oxoethylene, 1-oxotrimethylene, 2-oxotrimethylene, 1-oxotetramethylene, 2-oxotetramethylene, and the like.

"Aryl" includes phenyl, naphthyl, and the like.

"Heteroaryl" refers to 5- or 6-membered monocylic heteroaromatic group which contains 1 or more than 2, preferably 1 to 3 hetero atoms identically or differently selected from the group of oxygen atom, nitrogen atom and sulfur atom; or condensed heteroaromatic group, where the aforesaid monocylic heteroaromatic group is condensed with the aforesaid aryl group, or with the identified or different aforesaid monocylic heteroaromatic group each other, for example, pyrrolyl, furyl, thienyl, imidazolyl, pyrazolyl, thiazolyl, isothiazolyl, oxazolyl, isoxazolyl, 1,2,3-triazolyl, 1,2,4-triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazyl, naphthylidinyl, quinoxalinyl, quinazolinyl, cinnolinyl, pteridinyl, pyrido[3,2-b]pyridyl, and the like.

"Lower alkylamino" refers to an amino group monosubstituted with the aforesaid lower alkyl, for example, methylamino, ethylamino, propylamino, isopropylamino, butylamino, sec-butylamino, tert-butylamino, and the like.

"Di-lower alkylamino" refers to an amino group di-substituted with identical or different aforesaid lower alkyl, for example, dimethylamino, diethylamino, ethylmethylamino, dipropylamino, methylpropylamino, diisopropylamino, and the like.

The salts of compounds of formula (I) refer to the pharmaceutically acceptable and common salts, for example, base addition salt to carboxyl group when the compound has a carboxyl group, or acid addition salt to amino or basic heterocyclyl when the compound has an amino or basic heterocyclyl group, and the like.

Aforesaid base addition salts include salts with alkali metals (for example sodium, potassium); alkaline earth metals (for example calcium, magnesium); ammonium or organic amines (for example trimethylamine, triethylamine, dicyclohexylamine, ethanolamine, diethanolamine, triethanolamine, procaine, N,N'-dibenzylethylenediamine), and the like.

Aforesaid acid addition salts include salts with inorganic acids (for example hydrochloric acid, sulfuric acid, nitric acid, phosphoric acid, perchloric acid), organic acids (for example maleic acid, fumaric acid, tartaric acid, citric acid, ascorbic acid, trifluoroacetic acid), sulfonic acids (for example methanesulfonic acid, isethionic acid, benzenesulfonic acid, p-toluenesulfonic acid), and the like.

The esters of compounds of formula (I) refer to, for example, the pharmaceutically acceptable, common esters on carboxyl group when the compound has a carboxyl group, for example, esters with lower alkyls (for example methyl, ethyl, propyl, isopropyl, butyl, sec-butyl, tert-butyl, pentyl, isopentyl, neopentyl, cyclopropyl, cyclobutyl, cyclopentyl), aralkyls (for example benzyl, phenethyl), lower alkenyls (for example allyl, 2-butenyl), lower alkoxy (lower) alkyls (for example methoxymethyl, 2-methoxyethyl, 2-ethoxyethyl), lower alkanoyloxy (lower) alkyls (for example acetoxymethyl, pivaloyloxy-methyl, 1-pivaloyloxyethyl), lower alkoxycarbonyl (lower) alkyls (for example methoxycarbonylmethyl, isopropoxycarbonylmethyl), carboxy-(lower)alkyls (for example carboxymethyl), lower alkoxycarbonyloxy-(lower)alkyls (for example 1-(ethoxycarbonyloxy)ethyl, 1-(cyclohexyl-oxycarbonyloxy)ethyl), carbamoyloxy(lower)alkyls (for example carbamoyloxymethyl), phthalidyl group, (5-substituted-2-oxo-1,3-dioxol-4-yl)methyl (for example (5-methyl-2-oxo-1,3-dioxol-4-yl)methyl), and the like.

An N-oxide derivative of the compound represented by the formula (I) means a compound of which any one or more than one nitrogen atoms present in the compound of the formula (I) is or are oxidized to form an N-oxide or N-oxides, and such an N-oxide derivative includes, for example, a compound of which nitrogen atom is oxidized in case when T, U, V or/and W in the formula (I) is or are nitrogen.

"An agent for treatment" refers to a medicament which is employed for the treatment and/or prophylaxis of various diseases.

In order to disclose the aforesaid compounds of the general formula (I) more detailed, the various symbols used in the formula (I) are explained in more detail by the use of preferred embodiments.

$Ar^1$ represents aryl or heteroaryl which may be substituted, the substituent being selected from the group consisting of hydroxy, halogen, nitro, lower alkyl, halo(lower) alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of -Q-$Ar^2$.

"Aryl or heteroaryl which may be substituted, the substituent being selected from the group consisting of hydroxy, halogen, nitro, lower alkyl, halo(lower)alkyl, hydroxy(lower)alkyl, cyclo(lower)alkyl, lower alkenyl, lower alkoxy, halo(lower) alkoxy, lower alkylthio, carboxyl, lower alkanoyl, lower alkoxycarbonyl, lower alkylene optionally substituted with oxo, and a group represented by formula of -Q-$Ar^2$" refers to unsubstituted aforesaid aryl or aforesaid heteroaryl, or the aforesaid aryl or aforesaid heteroaryl which has substituent(s) at the substitutable, arbitrary position(s). The aforesaid substituent can be, identically or differently, one or not less than 2, preferably 1 or 2 selected from the group consisting of hydroxy, halogen, nitro, lower alkyl, halo(lower)alkyl, hydroxy(lower)alkyl, cyclo(lower) alkyl, lower alkenyl, lower alkoxy, halo(lower)alkoxy, lower alkylthio, carboxyl, lower alkanoyl, lower alkoxycarbonyl, lower alkylene optionally substituted with oxo, and a group of formula: -Q-$Ar^2$.

Halogen atom as the aforesaid substituent includes fluorine atom, chlorine atom, and the like preferably.

Lower alkyl as the aforesaid substituent includes methyl, ethyl, propyl, isopropyl, and the like preferably.

Halo(lower)alkyl as the aforesaid substituent includes difluoromethyl, trifluoromethyl, and the like preferably.

Hydroxy(lower)alkyl as the aforesaid substituent includes hydroxymethyl, 2-hydroxyethyl, 1-hydroxy-1-methylethyl, and the like preferably.

Cyclo(lower)alkyl as the aforesaid substituent includes cyclopropyl, cyclobutyl, and the like preferably.

Lower alkenyl as the aforesaid substituent includes vinyl, 1-propenyl, 2-methyl-1-propenyl, and the like preferably.

Lower alkoxy as the aforesaid substituent includes methoxy, ethoxy, and the like preferably.

Halo(lower)alkoxy as the aforesaid substituents includes fluoromethoxy, difluoromethoxy, trifluoromethoxy, and the like preferably.

Lower alkylthio as the aforesaid substituent includes methylthio, ethylthio, and the like preferably.

Lower alkanoyl as the aforesaid substituent includes acetyl, propionyl, and the like preferably.

Lower alkoxycarbonyl as the aforesaid substituent includes methoxycarbonyl, ethoxycarbonyl, and the like preferably.

Lower alkylene optionally substituted with oxo as the aforesaid substituent includes 1-oxotetramethylene, and the like preferably.

In a group of formula: -Q-$Ar^2$ as the aforesaid substituent, $Ar^2$ represents aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl; Q represents a single bond or carbonyl.

"Aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl" refers to unsubstituted aforesaid aryl or aforesaid heteroaryl, or the aforesaid aryl or aforesaid heteroaryl which has substituent(s) at the substitutable, arbitrary position(s). The aforesaid substituent can be, identically or differently, one or not less than 2, preferably 1 or 2 selected from the group consisting of halogen, cyano, lower alkyl, halo(lower)alkyl, hydroxy(lower)alkyl, hydroxy, lower alkoxy, halo(lower) alkoxy, lower alkylamino, di-lower alkylamino, lower alkanoyl and aryl.

Halogen atom as the aforesaid substituent includes, preferably, fluorine atom, chlorine atom, and the like.

Lower alkyl as the aforesaid substituent includes, preferably, methyl, ethyl, propyl, isopropyl, and the like.

Halo(lower)alkyl as the aforesaid substituent includes, preferably, difluoromethyl, trifluoromethyl, and the like.

Hydroxy(lower)alkyl as the aforesaid substituent includes, preferably, hydroxymethyl, 2-hydroxyethyl, 1-hydroxy-1-methylethyl, and the like.

Lower alkoxy as the aforesaid substituent includes, preferably, methoxy, ethoxy, and the like.

Halo(lower)alkoxy as the aforesaid substituent includes, preferably, fluoromethoxy, difluoromethoxy, trifluoromethoxy, and the like.

Lower alkylamino as the aforesaid substituent includes, preferably, methylamino, ethylamino, and the like.

Di-lower alkylamino as the aforesaid substituent includes, preferably, dimethylamino, diethylamino, and the like.

Lower alkanoyl as the aforesaid substituent includes, preferably, acetyl, propionyl, and the like.

Aryl as the aforesaid substituent includes, preferably, phenyl, and the like.

The substituent(s) of $Ar^2$ include, preferably, halogen, cyano, lower alkyl, halo(lower)alkyl, hydroxy(lower)alkyl, hydroxy, halo(lower)alkoxy, and the like.

Aryl in $Ar^2$ includes, preferably, phenyl, and the like and heteroaryl includes imidazolyl, pyridyl, benzofuranyl, quinolyl, and the like.

Consequently, a group of formula: -Q-$Ar^2$ includes, for example, phenyl, 2-fluorophenyl, 3-fluorophenyl, 4-fluorophenyl, 2,3-difluorophenyl, 2,4-difluorophenyl, 3,5-difluorophenyl, 2-chlorophenyl, 3-chlorophenyl, 4-chlorophenyl, 2-cyanophenyl, 3-cyanophenyl, 4-cyanophenyl, 2-methylphenyl, 3-methylphenyl, 4-methylphenyl, 2-fluoro-5-methylphenyl, 3-fluoromethylphenyl, 2-trifluoromethylphenyl, 3-trifluoromethylphenyl, 4-trifluoromethylphenyl, 2-fluoro-4-hydroxyphenyl, 2-fluoro-3,4-dihydroxyphenyl, 2-fluoro-4,5-dihydroxyphenyl, 2-fluoro-4,6-dihydroxyphenyl, 2-methoxyphenyl, 3-methoxyphenyl, 4-methoxyphenyl, 3-fluoro-5-methoxyphenyl, 3-fluoromethoxyphenyl, 3-difluoromethoxyphenyl, 3-(2-hydroxyethyl)phenyl, 3-hydroxymethylphenyl, 3-(1-hydroxy-1-methylethyl)phenyl, 3-hydroxyphenyl, 4-hydroxyphenyl, 2-imidazolyl, 1-ethyl-2-imidazolyl, 1,2,4-thiadiazol-5-yl, 1,3,4-thiadiaol-2-yl, 2-pyridyl, 3-pyridyl, 4-pyridyl, 2-ethyl-4-pyridyl, 4-pyrimidinyl, 5-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 8-quinolyl, benzoyl, 2-pyridylcarbonyl, and the like, and preferably, phenyl, 2-fluorophenyl, 3-fluorophenyl, 3,5-difluorophenyl, 3-chlorophenyl, 4-chlorophenyl, 3-cyanophenyl, 3-trifluoromethylphenyl, 3-difluoromethoxyphenyl, 3-(2-hydroxyethyl)phenyl, 3-hydroxyphenyl, 4-hydroxyphenyl, 1-ethyl-2-imidazolyl, 2-pyridyl, 7-benzo[b]furanyl, 2-quinolyl, 3-quinolyl, benzoyl, 2-pyridylcarbonyl, and the like.

The substituent of $Ar^1$ includes, preferably, hydroxy, halogen, lower alkyl, halo(lower)alkyl, lower alkenyl, lower alkanoyl, lower alkylene optionally substituted with oxo, and a group of formula: -Q-$Ar^2$, and the like.

Aryl in $Ar^1$ includes, preferably, phenyl, and the like and heteroaryl of $Ar^1$ includes pyrrolyl, imidazolyl, pyrazolyl, thiazolyl, oxazolyl, isoxazolyl, 1,2,3-triazolyl, 1,2,4-thiadiazolyl, pyridyl, pyrazinyl, pyrimidinyl, 1,2,4-triazinyl, benzoxazolyl, benzothiazolyl, quinolyl, pyrido[3,2-b]pyridyl, and the like.

Consequently, Ar¹ includes, for example, 3-fluorophenyl, 4-fluorophenyl, 3,4-difluorophenyl, 3-chlorophenyl, 4-chlorophenyl, 3,4-dichlorophenyl, 4-acetylphenyl, 5-oxo-5,6,7,8-tetrahydro-2-naphthyl, 4-acetyl-3-trifluoromethylphenyl, 4-(1-ethyl-2-imidazolyl)phenyl, 3-(2-pyridyl)phenyl, 3-(4-pyridyl)phenyl, 4-(2-pyridyl)phenyl, 4-(3-pyridyl)phenyl, 4-(2-ethyl-4-pyridyl)phenyl, 4-(4-pyrimidinyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3-fluorophenyl)-4-imidazolyl, 1-(4-fluorophenyl)-4-imidazolyl, 1-(2,3-difluorophenyl)-4-imidazolyl, 1-(2,4-difluorophenyl)-4-imidazolyl, 1-(3,5-difluorophenyl)-4-imidazolyl, 1-(3-chlorophenyl)-4-imidazolyl, 1-(2-cyanophenyl)-4-imidazolyl, 1-(3-cyanophenyl)-4-imidazolyl, 1-(4-cyanophenyl)-4-imidazolyl, 1-(3-trifluoromethylphenyl)-4-imidazolyl, 1-[3-(2-hydroxyethyl)phenyl]-4-imidazolyl, 1-[3-(1-hydroxy-1-methylethyl)phenyl]-4-imidazolyl, 1-(4-hydroxyphenyl)-4-imidazolyl, 1-(3-methoxyphenyl)-4-imidazolyl, 1-(2-difluoromethoxyphenyl)-4-imidazolyl, 1-(3-difluoromethoxyphenyl)-4-imidazolyl, 1-(4-difluoromethoxy-phenyl)-4-imidazolyl, 1-(2-pyridyl)-4-imidazolyl, 1-(4-benzo[b]furanyl)-4-imidazolyl, 1-(5-benzo[b]furanyl)-4-imidazolyl, 1-(7-benzo[b]furanyl)-4-imidazolyl, 1-(2-quinolyl)-4-imidazolyl, 1-(3-quinolyl)-4-imidazolyl, 1-(4-quinolyl)-4-imidazolyl, 1-(5-quinolyl)-4-imidazolyl, 1-(6-quinolyl)-4-imidazolyl, 1-(8-quinolyl)-4-imidazolyl, 1-phenyl-3-pyrazolyl, 5-phenyl-3-pyrazolyl, 1-phenyl-4-pyrazolyl, 1-(2-fluorophenyl)-3-pyrazolyl, 1-(2-fluoro-4-hydroxyphenyl)-3-pyrazolyl, 1-(2-fluoro-3,4-dihydroxyphenyl)-3-pyrazolyl, 1-(2-fluoro-4,5-dihydroxyphenyl)-3-pyrazolyl, 1-(2-fluoro-4,6-dihydroxyphenyl)-3-pyrazolyl, 5-(2-fluorophenyl)-3-pyrazolyl, 5-(3-fluorophenyl)-3-pyrazolyl, 1-(3-fluorophenyl)-4-pyrazolyl, 1-(4-fluorophenyl)-3-pyrazolyl, 5-(4-fluorophenyl)-3-pyrazolyl, 5-(2-chlorophenyl)-3-pyrazolyl, 5-(3-chlorophenyl)-3-pyrazolyl, 5-(4-chlorophenyl)-3-pyrazolyl, 5-(2-difluoromethoxyphenyl)-3-pyrazolyl, 5-(3-difluoromethoxyphenyl)-3-pyrazolyl, 2-methyl-5-phenyl-3-pyrazolyl, 5-(2-pyridyl)-3-pyrazolyl, 5-(2-quinolyl)-3-pyrazolyl, 5-(3-quinolyl)-3-pyrazolyl, 4-hydroxy-1-phenyl-3-pyrazolyl, 1-(2-fluorophenyl)-4-hydroxy-3-pyrazolyl, 1-(4-fluorophenyl)-4-hydroxy-3-pyrazolyl, 4-phenyl-2-thiazolyl, 5-phenyl-2-thiazolyl, 5-(3-chlorophenyl)-2-thiazolyl, 5-(4-chlorophenyl)-2-thiazolyl, 5-(4-methoxyphenyl)-2-thiazolyl, 5-(2-pyridyl)-2-thiazolyl, 2-phenyl-4-thiazolyl, 4-phenyl-2-oxazolyl, 5-phenyl-2-oxazolyl, 4-(2-fluoromethoxyphenyl)-2-oxazolyl, 4-(3-fluoromethoxyphenyl)-2-oxazolyl, 5-phenyl-3-isoxazolyl, 3-phenyl-5-isoxazolyl, 3-(2-chlorophenyl)-5-isoxazolyl, 3-(3-chlorophenyl)-5-isoxazolyl, 3-(4-chlorophenyl)-5-isoxazolyl, 3-(2-pyridyl)-5-isoxazolyl, 2-phenyl-1,2,3-triazol-4-yl, 5-phenyl-1,2,4-thiadiazol-3-yl, 5-phenyl-1,3,4-thiadiazol-2-yl, 5-(3-chlorophenyl)-1,3,4-thiadiazol-2-yl, 5-(2-pyridyl)-1,3,4-thiadiazol-2-yl, 5-(2-ethyl-4-pyridyl)-1,3,4-thiadiazol-2-yl, 5-phenyl-2-pyridyl, 6-phenyl-3-pyridyl, 2-phenyl-4-pyridyl, 5-(2-pyridyl)-2-pyridyl, 5-benzoyl-2-pyridyl, 6-benzoyl-3-pyridyl, 5-chloro-2-pyrazinyl, 5-(2-methyl-1-propenyl)-2-pyrazinyl, 5-acetyl-2-pyrazinyl, 5-propionyl-2-pyrazinyl, 5-phenyl-2-pyrazinyl, 5-(3-hydroxyphenyl)-2-pyrazinyl, 5-(4-hydroxyphenyl)-2-pyrazinyl, 5-(1,2,4-thiadiazol-5-yl)-2-pyrazinyl, 5-(1,3,4-thiadiazol-2-yl)-2-pyrazinyl, 5-(2-pyridyl)-2-pyrazinyl, 5-(3-pyridyl)-2-pyrazinyl, 5-(5-pyrimidinyl)-2-pyrazinyl, 5-(3-quinolyl)-2-pyrazinyl, 5-benzoyl-2-pyrazinyl, 5-(2-pyridylcarbonyl)-2-pyrazinyl, 5-acetyl-2-pyrimidinyl, 5-acetyl-3-methyl-2-pyrimidinyl, 4-phenyl-2-pyrimidinyl, 5-phenyl-2-pyrimidinyl, 6-phenyl-4-pyrimidinyl, 2-phenyl-5-pyrimidinyl, 5-(2-fluorophenyl)-2-pyrimidinyl, 5-(3-fluorophenyl)-2-pyrimidinyl, 5-(4-fluorophenyl)-2-pyrimidinyl, 5-(2-chlorophenyl)-2-pyrimidinyl, 5-(3-chlorophenyl)-2-pyrimidinyl, 5-(4-chlorophenyl)-2-pyrimidinyl, 5-(2-methylphenyl)-2-pyrimidinyl, 5-(3-methylphenyl)-2-pyrimidinyl, 5-(2-fluoromethylphenyl)-2-pyrimidinyl, 5-(3-fluoromethylphenyl)-2-pyrimidinyl, 5-(2-trifluoromethylphenyl)-2-pyrimidinyl, 5-(3-trifluoromethylphenyl)-2-pyrimidinyl, 5-(4-trifluoromethylphenyl)-2-pyrimidinyl, 5-(2-hydroxymethylphenyl)-2-pyrimidinyl, 5-(3-hydroxymethylphenyl)-2-pyrimidinyl, 5-(2-hydroxyphenyl)-2-pyrimidinyl, 5-(3-hydroxyphenyl)-2-pyrimidinyl, 5-(4-hydroxyphenyl)-2-pyrimidinyl, 5-(2-methoxyphenyl)-2-pyrimidinyl, 5-(3-methoxyphenyl)-2-pyrimidinyl, 5-(4-methoxyphenyl)-2-pyrimidinyl, 5-(2-fluoromethoxyphenyl)-2-pyrimidinyl, 5-(3-fluoromethoxyphenyl)-2-pyrimidinyl, 5-(2-fluoro-5-methylphenyl)-2-pyrimidinyl, 5-(3-fluoro-5-methoxyphenyl)-2-pyrimidinyl, 6-phenyl-3-pyridazinyl, 6-phenyl-1,2,4-triazin-3-yl, 5-chloro-2-benzoxazolyl, 5-fluoro-2-benzothiazolyl, 4-methyl-2-benzothiazolyl, 2-methyl-5-benzothiazolyl, 4-methoxy-2-benzothiazolyl, 3-quinolyl, 6-quinolyl, 7-methyl-2-quinolyl, 2-methyl-6-quinolyl, 6-chloro-2-quinoxalinyl, pyrido[3,2-b]pyridin-2-yl, 7-chloropyrido[3,2-b]pyridin-2-yl, 7-methylpyrido[3,2-b]pyridin-2-yl, 7-trifluoromethylpyrido[3,2-b]pyridin-2-yl, 7-difluoromethoxypyrido[3,2-b]pyridin-2-yl, 7-acetylpyrido[3,2-b]pyridin-2-yl, and the like, preferably 3,4-dichlorophenyl, 4-acetylphenyl, 5-oxo-5,6,7,8-tetrahydro-2-naphthyl, 4-acetyl-3-trifluoromethylphenyl, 4-(1-ethyl-2-imidazolyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3,5-difluorophenyl)-4-imidazolyl, 1-(3-chlorophenyl)-4-imidazolyl, 1-(3-cyanophenyl)-4-imidazolyl, 1-[3-(2-hydroxyethyl)phenyl]-4-imidazolyl, 1-(4-hydroxyphenyl)-4-imidazolyl, 1-(3-difluoromethoxyphenyl)-4-imidazolyl, 1-(7-benzo[b]furanyl)-4-imidazolyl, 1-(2-quinolyl)-4-imidazolyl, 1-(3-quinolyl)-4-imidazolyl, 1-phenyl-3-pyrazolyl, 5-phenyl-3-pyrazolyl, 1-phenyl-4-pyrazolyl, 1-(2-fluoro-4-hydroxyphenyl)-3-pyrazolyl, 1-(2-fluoro-3,4-dihydroxyphenyl)-3-pyrazolyl, 1-(2-fluoro-4,5-dihydroxyphenyl)-3-pyrazolyl, 1-(2-fluoro-4,6-dihydroxyphenyl)-3-pyrazolyl, 1-(3-fluorophenyl)-4-pyrazolyl, 1-(4-fluorophenyl)-3-pyrazolyl, 5-(4-chlorophenyl)-3-pyrazolyl, 5-(3-quinolyl)-3-pyrazolyl, 4-hydroxy-1-phenyl-3-pyrazolyl, 1-(2-fluorophenyl)-4-hydroxy-3-pyrazolyl, 1-(4-fluorophenyl)-4-hydroxy-3-pyrazolyl, 5-phenyl-2-thiazolyl, 3-phenyl-5-isoxazolyl, 5-(2-methyl-1-propenyl)-2-pyrazinyl, 5-phenyl-2-pyrazinyl, 5-(3-hydroxyphenyl)-2-pyrazinyl, 5-(4-hydroxyphenyl)-2-pyrazinyl, 5-(2-pyridyl)-2-pyrazinyl, 5-benzoyl-2-pyrazinyl, 5-phenyl-2-pyrimidinyl, 5-(2-fluorophenyl)-2-pyrimidinyl, 5-(3-fluorophenyl)-2-pyrimidinyl, 5-(3-chlorophenyl)-2-pyrimidinyl, 5-(3-trifluoromethyl-phenyl)-2-pyrimidinyl, 5-(4-hydroxyphenyl)-2-pyrimidinyl, 5-chloro-2-benzoxazolyl, 4-methyl-2-benzothiazolyl, 7-methyl-2-quinolyl, 7-trifluoromethylpyrido[3,2-b]pyridin-2-yl, and the like, especially 1-(4-hydroxyphenyl)-4-imidazolyl, 1-phenyl-3-pyrazolyl, 5-phenyl-3-pyrazolyl, 1-(2-fluoro-4-hydroxyphenyl)-3-pyrazolyl, 1-(2-fluoro-3,4-dihydroxyphenyl)-3-pyrazolyl, 1-(2-fluoro-4,5-dihydroxyphenyl)-3-pyrazolyl, 1-(2-fluoro-4,6-dihydroxyphenyl)-3-pyrazolyl, 4-hydroxy-1-phenyl-3-pyrazolyl, 1-(2-fluorophenyl)-4-hydroxy-3-pyrazolyl, 1-(4-fluorophenyl)-4-hydroxy-3-pyrazolyl, 5-phenyl-2-pyrazinyl, 5-(3-hydroxyphenyl)-2-pyrazinyl, 5-(4-hydroxyphenyl)-2-pyrazinyl, 5-phenyl-2-pyrimidinyl, 5-(2-fluorophenyl)-2- pyrimidinyl, 5-(3-fluorophenyl)-2-pyrimidinyl, 5-(4-hydroxyphenyl)-2-pyrimidinyl, 7-trifluoro-methylpyrido[3,2-b]pyridin-2-yl, and the like.

n represents 0 or 1, 0 is preferable.

T, U, V and W represent independently nitrogen atom or methine which may have a substituent selected from the group consisting of halogen, lower alkyl, hydroxy and lower alkoxy, where at least two of them represent the said methine group.

"Methine which may have a substituent selected from the group consisting of halogen, lower alkyl, hydroxy and lower alkoxy" refers to unsubstituted methine or methine having a substituent which can be selected from the group consisting of halogen, lower alkyl, hydroxy and lower alkoxy.

Halogen atom as the aforesaid substituent includes preferably fluorine atom, chlorine atom, and the like.

Lower alkyl as the aforesaid substituent includes preferably methyl, ethyl, and the like.

Lower alkoxy as the aforesaid substituent includes preferably methoxy, ethoxy, and the like.

The aforesaid substituent include preferably halogen, and the like.

The preferred mode of T, U, V and W includes, for example, T, U, V and W are independently methine optionally having the aforesaid substituent, preferably halogen; or one of T, U, V and W is nitrogen atom.

X represents methine, hydroxy substituted methine or nitrogen.

Y represents imino which may be substituted with lower alkyl, or oxygen.

"Imino which may be substituted with lower alkyl" refers to unsubstituted imino or imino substituted with lower alkyl.

The aforesaid lower alkyl includes, preferably, methyl, ethyl, and the like.

Y is preferably unsubstituted imino or oxygen, especially oxygen.

In more detail, a group of formula (15):

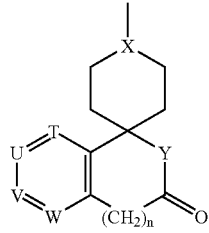

(15)

includes a group of formula (16):

(16)

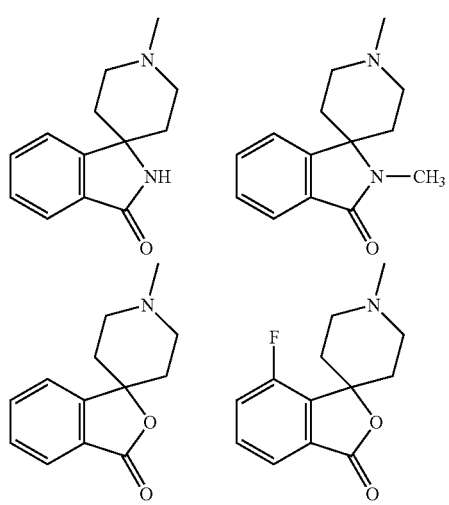

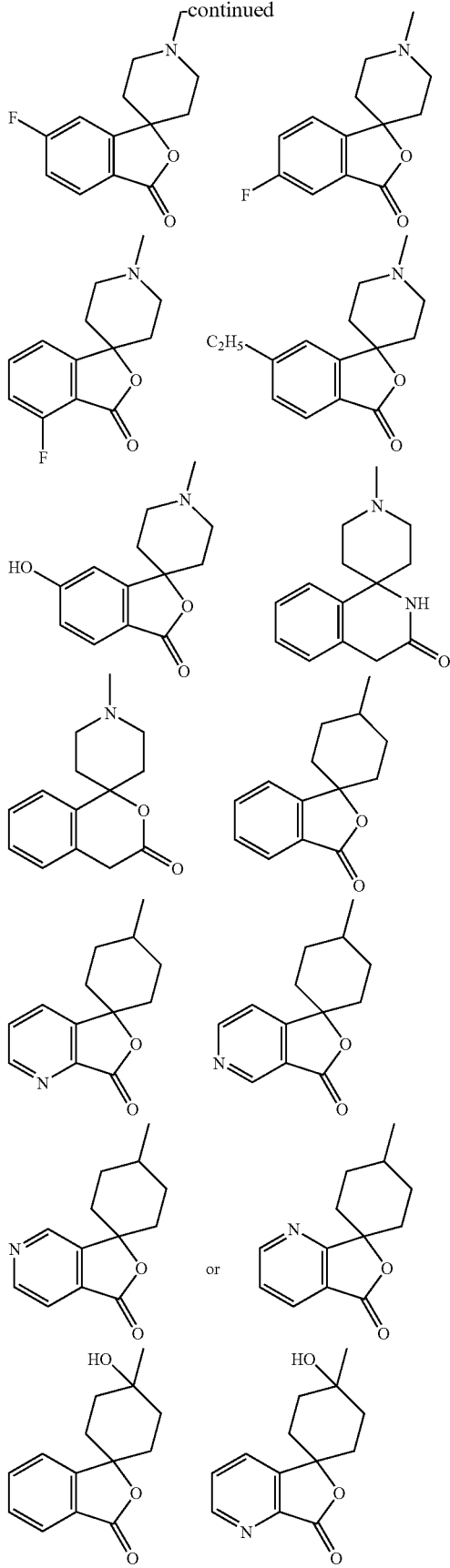

-continued

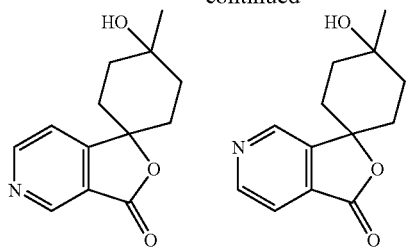
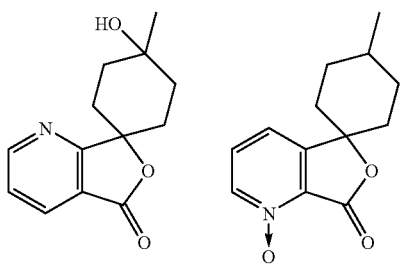
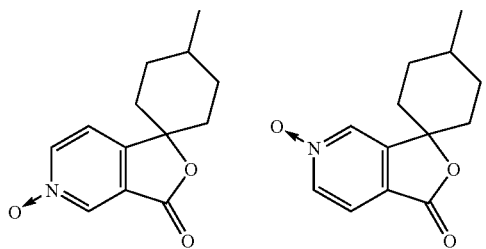
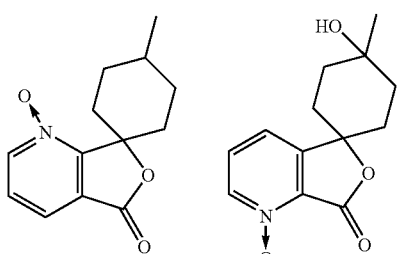
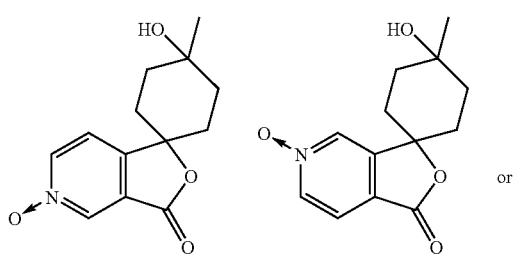
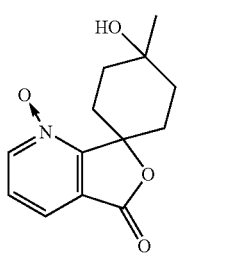

and the like.

Preferred compounds of the general formula (I) are, for example, compounds of the general formula (I-a):

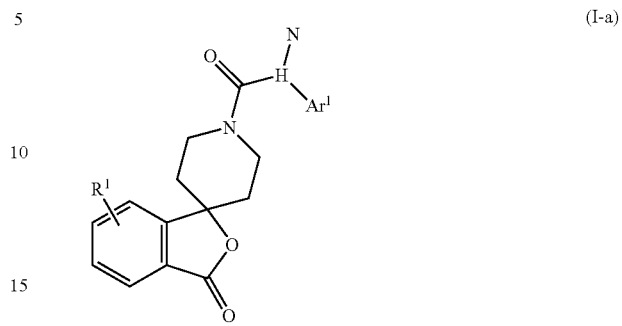

(I-a)

wherein $R^1$ represents hydrogen atom or halogen, $Ar^1$ has the aforesaid meaning;

or compounds of the general formula (I-b):

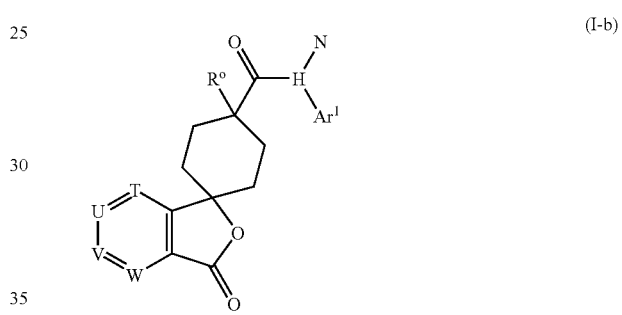

(I-b)

wherein $R^o$ represents hydrogen or hydroxy; and $Ar^1$, T, U, V and W have the aforesaid meanings.

With regard to the compound represented by the general formula (I-a), the preferred compounds are, for example, the compounds, wherein the aryl group in $Ar^1$ is phenyl, or the heteroaryl group in $Ar^1$ is imidazolyl, pyrazolyl, isoxazolyl, 1,2,4-thiadiazolyl, pyrazinyl, pyrimidinyl, quinolyl or pyrido[3,2-b]pyridyl.

With regard to the compound represented by the general formula (I-b), the preferred compounds are, for example, the compounds, wherein the aryl group in $Ar^1$ is phenyl, or the heteroaryl group in $Ar^1$ is pyrrolyl, imidazolyl, pyrazolyl, thiazolyl, oxazolyl, isoxazolyl, 1,2,3-triazolyl, 1,2,4-thiadiazolyl, pyridyl, pyrazinyl, pyrimidinyl or 1,2,4-triazinyl.

Further, with regard to the compound represented by the general formula (I-b), the preferred compounds are, for example, the compounds, wherein one of T, U, V and W is a nitrogen atom and the more preferred compounds are, for example, the compounds wherein V is a nitrogen atom and T,U as well as W are an unsubstituted methine group.

Compounds of this invention may include stereoisomers such as optical isomers, diastereoisomers and geometrical isomers, or tautomers depending upon the mode of substituents. Compounds of this invention include all the stereoisomers, tautomers and their mixtures.

For example, compounds of the general formula (I-b) include stereoisomers such as trans-form compound of the general formula (I-1b) or (I-3b):

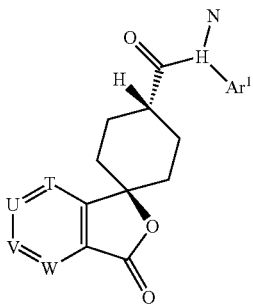

(I-1b)

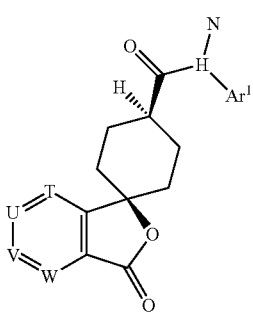

(I-3b)

and cis-form compound of the general formula (I-2b) or (I-4b):

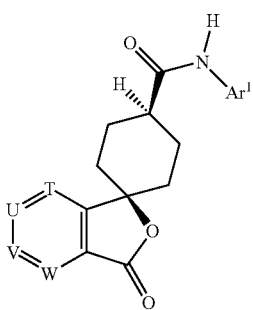

(I-2b)

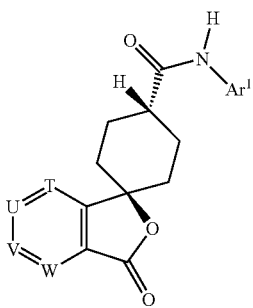

(I-4b)

The stereoisomers such as the general formula (I-1b) or (I-4b) are preferable.

Also included within the scope of the invention are polymorphs, hydrates and solvates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The specific compound represented by the general formula (I) is, for example, cis-N-(4-benzoylphenyl)-4-hydroxy-3'-oxospiro[cyclohexane-1,1'(3'H)-isobenzofuran]-4-carboxamide, cis-4-hydroxy-3'-oxo-N-(5-phenyl-2-pyrazinyl)spiro[cyclohexane-1,1'(3'H)-isobenzofuran]-4-carboxamide, cis-4-hydroxy-N-[5-(4-hydroxyphenyl)-2-pyrazinyl]-3'-oxospiro[cyclohexane-1,1'(3'H)-isobenzofuran]-4-carboxamide, cis-4-hydroxy-3'-oxo-N-(1-phenyl-4-imidazolyl)spiro[cyclohexane-1,1'(3'H)-isobenzofuran]-4-carboxamide, cis-4-hydroxy-N-[1-(4-hydroxyphenyl)-4-imidazolyl]-3'-oxospiro[cyclohexane-1,1'(3'H)-isobenzofuran]-4-carboxamide, cis-4-hydroxy-3'-oxo-N-(5-phenyl-2-pyrimidinyl)-spiro[cyclohexane-1,1'(3'H)-isobenzofuran]-4-carboxamide, cis-4-hydroxy-3'-oxo-N-[5-(4-hydroxyphenyl)-2-pyrimidinyl]-spiro[cyclohexane-1,1'(3'H)-isobenzofuran]-4-carboxamide, cis-N-[1-(3,5-difluorophenyl)-4-imidazolyl]-4-hydroxy-3'-oxospiro[cyclohexane-1,1'(3'H)-isobenzofuran]-4-carboxamide, cis-4-hydroxy-3'-oxo-N-(5-phenyl-3-pyrazolyl)spiro[cyclohexane-1,1'(3'H)-isobenzofuran]-4-carboxamide, cis-N-[1-(2-fluorophenyl)-4-imidazolyl]-4-hydroxy-3'-oxospiro[cyclohexane-1,1'(3'H)-isobenzofuran]-4-carboxamide, cis-N-(4-acetyl-3-trifluoromethylphenyl)-4-hydroxy-3'-oxospiro[cyclohexane-1,1'(3'H)-isobenzofuran]-4-carboxamide, cis-4-hydroxy-3'-oxo-N-[1-(3-quinolyl)-4-imidazolyl]spiro[cyclohexane-1,1'(3'H)-isobenzofuran]-4-carboxamide, cis-N-[1-(3-cyanophenyl)-4-imidazolyl]-4-hydroxy-3'-oxospiro[cyclohexane-1,1'(3'H)-isobenzofuran]-4-carboxamide, cis-N-(4-benzoylphenyl)-4'-hydroxy-3-oxospiro[4-azaisobenzofuran-1(3H),1'-cyclohexane]-4'-carboxamide, cis-4'-hydroxy-3-oxo-N-(5-phenyl-2-pyrazinyl)spiro[4-azaisobenzofuran-1(3H),1'-cyclohexane]-4'-carboxamide, trans-3-oxo-N-(5-phenyl-2-pyrazinyl)spiro[4-azaisobenzofuran-1(3H),1'-cyclohexane]-4'-carboxamide 4-oxide, cis-4'-hydroxy-3-oxo-N-(5-phenyl-2-pyrazinyl)spiro[4-azaisobenzofuran-1(3H),1'-cyclohexane]-4'-carboxamide 4-oxide, cis-4'-hydroxy-3-oxo-N-(3-phenyl-5-isoxazolyl)spiro[4-azaisobenzofuran-1(3H),1'-cyclohexane]-4'-carboxamide, trans-3-oxo-N-(3-phenyl-5-isoxazolyl)spiro[4-azaisobenzofuran-1(3H),1'-cyclohexane]-4'-carboxamide 4-oxide, cis-4'-hydroxy-3-oxo-N-(5-phenyl-2-pyrimidinyl)spiro[4-azaisobenzofuran-1(3H),1'-cyclohexane]-4'-carboxamide 4-oxide, cis-N-(4-benzoylphenyl)-4'-hydroxy-3-oxospiro[5-azaisobenzofuran-1(3H),1'-cyclohexane]-4'-carboxamide, trans-N-(4-benzoylphenyl)-3-oxospiro[5-azaisobenzofuran-1(3H),1'-cyclohexane]-4'-carboxamide 5-oxide, cis-N-(4-benzoylphenyl)-4'-hydroxy-3-oxospiro[5-azaisobenzofuran-1(3H),1'-cyclohexane]-4'-carboxamide 5-oxide, cis-N-(4-benzoylphenyl)-4'-hydroxy-3-oxospiro[6-azaisobenzofuran-1(3H),1'-cyclohexane]-4'-carboxamide, trans-N-(4-benzoylphenyl)-3-oxospiro[6-azaisobenzofuran-1(3H),1'-cyclohexane]-4'-carboxamide 6-oxide, cis-N-(4-benzoylphenyl)-4'-hydroxy-3-oxospiro[6-azaisobenzofuran-1(3H),1'-cyclohexane]-4'-carboxamide 6-oxide, cis-4'-hydroxy-3-oxo-N-(5-phenyl-2-pyrimidinyl)spiro[5- azaisobenzofuran-1(3H),1'-cyclohexane]-4'-carboxamide, trans-3-oxo-N-(5-phenyl-2-pyrimidinyl)spiro[5-azaisobenzofuran-1(3H),1'-cyclohexane]-4'-carboxamide 5-oxide, cis-4'-hydroxy-3-oxo-N-(5-phenyl-2-pyrimidinyl)spiro[5-azaisobenzofuran-1(3H),1'-cyclohexane]-4'-carboxamide 5-oxide, cis-N-[5-(3-fluorophenyl)-2-pyrimidinyl]-4'-hydroxy-3-oxospiro[5-azaisobenzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide 5-oxide, cis-N-[5-(3-fluorophenyl)-2-pyrimidinyl]-4'-hydroxy-3-oxospiro[5-azaisobenzofuran-1(3H),1'-cyclohexane]-4'-carboxamide 5-oxide, cis-N-[5-(2-fluorophenyl)-2-pyrimidinyl]-4'-hydroxy-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide 5-oxide, cis-N-[5-(2-fluorophenyl)-2-pyrimidinyl]-4'-hydroxy-3-oxospiro[5-azaisobenzofuran-1(3H),1'-cyclohexane]-4'-carboxamide 5-oxide, cis-4'-hydroxy-3-oxo-N-(4-phenyl-2-oxazolyl)spiro[5-azaisobenzofuran-1(3H),1'-cyclohexane]-4'-carboxamide, trans-3-oxo-N-(4-phenyl-2-oxazolyl)spiro[5-azaisobenzofuran-1(3H),1'-cyclohexane]-4'-carboxamide 5-oxide, cis-4'-hydroxy-3-oxo-N-(4-phenyl-2-oxazolyl)spiro[5-azaisobenzofuran-1(3H),1'-cyclohexane]-4'-carboxamide 5-oxide, cis-N-[5-(2-methylphehyl)-2-pyrimidinyl]-4'-hydroxy-3-oxospiro[5-azaisobenzofuran-1(3H),1'-cyclohexane]-4'-carboxamide, trans-N-[5-(2-methylphenyl)-2-pyrimidinyl]-3-oxospiro[5-azaisobenzofuran-1(3H),1'-cyclohexane]-4'-carboxamide 5-oxide, cis-N-[5-(2-methylphenyl)-2-pyrimidinyl]-4'-hydroxy-3-oxospiro[5-azaisobenzofuran-1(3H),1'-cyclohexane]-4'-carboxamide 5-oxide, cis-N-[5-(3-methylphenyl)-2-pyrimidinyl]-4'-hydroxy-3-oxospiro[5-azaisobenzofuran-1(3H),1'-cyclohexane]-4-carboxamide, trans-N-[5-(3-methylphenyl)-2-pyrimidinyl]-3-oxospiro[5-azaisobenzofuran-1(3H),1'-cyclohexane]-4'-carboxamide 5-oxide, cis-N-[5-(3-methylphenyl)-2-pyrimidinyl]-4'-hydroxy-3-oxospiro[5-azaisobenzofuran-1(3H),1'-cyclohexane]-4'-carboxamide 5-oxide, cis-N-[5-(3-fluoromethoxyphenyl)-2-pyrimidinyl]-4'-hydroxy-3-oxospiro[5-azaisobenzofuran-1(3H),1'-cyclohexane]-4'-carboxamide, trans-N-[5-(3-fluoromethoxyphenyl)-2-pyrimidinyl]-3-oxospiro[5-azaisobenzofuran-1(3H),1'-cyclohexane]-4'-carboxamide 5-oxide, cis-N-[5-(3-fluoromethoxyphenyl)-2-pyrimidinyl]-4'-hydroxy-3-oxospiro[5-azaisobenzofuran-1(3H),1'-cyclohexane]-4'-carboxamide 5-oxide, cis-N-[5-(3-fluoromethylphenyl)-2-pyrimidinyl]-4'-hydroxy-3-oxospiro[5-azaisobenzofuran-1(3H),1'-cyclohexane]-4'-carboxamide, trans-N-[5-(3-fluoromethylphenyl)-2-pyrimidinyl]-3-oxospiro[5-azaisobenzofuran-1(3H),1'-cyclohexane]-4'-carboxamide 5-oxide, cis-N-[5-(3-fluoromethylphenyl)-2-pyrimidinyl]-4'-hydroxy-3-oxospiro[5-azaisobenzofuran-1(3H),1'-cyclohexane]-4'-carboxamide 5-oxide, cis-N-[5-(3-fluoro-5-methoxyphenyl)-2-pyrimidinyl]-4'-hydroxy-3-oxospiro[5-azaisobenzofuran-1(3H),1'-cyclohexane]-4'-carboxamide, trans-N-[5-(3-fluoro-5-methoxyphenyl)-2-pyrimidinyl]-3-oxospiro[5-azaisobenzofuran-1(3H),1'-cyclohexane]-4'-carboxamide 5-oxide, cis-N-[5-(3-fluoro-5-methoxyphenyl)-2-pyrimidinyl]-4'-hydroxy-3-oxospiro[5-azaisobenzofuran-1(3H),1'-cyclohexane]-4'-carboxamide 5-oxide, cis-N-[5-(2-fluoro-5-methylphenyl)-2-pyrimidinyl]-4'-hydroxy-3-oxospiro[5-azaisobenzofuran-1(3H),1'-cyclohexane]-4'-carboxamide, trans-N-[5-(2-fluoro-5-methylphenyl)-2-pyrimidinyl]-3-oxospiro[5-azaisobenzofuran-1(3H),1'-cyclohexane]-4'-carboxamide 5-oxide, cis-N-[5-(2-fluoro-5-methylphenyl)-2-pyrimidinyl]-4'-hydroxy-3-oxospiro[5-azaisobenzofuran-1(3H),1'-cyclohexane]-4'-carboxamide 5-oxide, cis-N-[4-(3-fluoromethoxyphenyl)-2-oxazolyl]-4'-hydroxy-3-oxospiro[5-azaisobenzofuran-1(3H),1'-cyclohexane]-4'-carboxamide, trans-N-[4-(3-fluoromethoxyphenyl)-2-oxazolyl]-3-oxospiro[5-azaisobenzofuran-1(3H),1'-cyclohexane]-4'-carboxamide 5-oxide, cis-N-[4-(3-fluoromethoxyphenyl)-2-oxazolyl]-4'-hydroxy-3-oxospiro[5-azaisobenzofuran-1(3H),1'-cyclohexane]-4'-carboxamide 5-oxide, cis-4'-hydroxy-N-[5-(3-hydroxymethylphenyl)-2-pyrimidinyl]-3-oxospiro[5-azaisobenzofuran-1(3H),1'-cyclohexane]-4'-carboxamide, trans-N-[5-(3-hydroxymethylphenyl)-2-pyrimidinyl]-3-oxospiro[5-azaisobenzofuran-1(3H),1'-cyclohexane]-4'-carboxamide 5-oxide, cis-4'-hydroxy-N-[5-(3-hydroxymethylphenyl)-2-pyrimidinyl]-3-oxospiro[5-azaisobenzofuran-1(3H),1'-cyclohexane]-4'-carboxamide 5-oxide, cis-4'-hydroxy-N-[5-(3-hydroxyphenyl)-2-pyrimidinyl]-3-oxospiro[5-azaisobenzofuran-1(3H),1'-cyclohexane]-4'-carboxamide, trans-N-[5-(3-hydroxyphenyl)-2-pyrimidinyl]-3-oxospiro[5-azaisobenzofuran-1(3H),1'-cyclohexane]-4'-carboxamide 5-oxide, cis-4'-hydroxy-N-[5-(3-hydroxyphenyl)-2-pyrimidinyl]-3-oxospiro[5-azaisobenzofuran-1(3H),1'-cyclohexane]-4'-carboxamide 5-oxide, cis-4'-hydroxy-3-oxo-N-(5-phenyl-2-pyrimidinyl)spiro[6-azaisobenzofuran-1(3H),1'-cyclohexane]-4'-carboxamide, trans-3-oxo-N-(5-phenyl-2-pyrimidinyl)spiro[6-azaisobenzofuran-1(3H),1'-cyclohexane]-4'-carboxamide 6-oxide, cis-4'-hydroxy-3-oxo-N-(5-phenyl-2-pyrimidinyl)spiro[6-azaisobenzofuran-1(3H),1'-cyclohexane]-4'-carboxamide 6-oxide, cis-N-[5-(3-fluoromethylphenyl)-2-pyrimidinyl]-4'-hydroxy-3-oxospiro[6-azaisobenzofuran-1(3H),1'-cyclohexane]-4'-carboxamide, trans-N-[5-(3-fluoromethylphenyl)-2-pyrimidinyl]-3-oxospiro[6-azaisobenzofuran-1(3H),1'-cyclohexane]-4'-carboxamide 6-oxide, cis-N-[5-(3-fluoromethylphenyl)-2-pyrimidinyl]-4'-hydroxy-3-oxospiro[6-azaisobenzofuran-1(3H),1'-cyclohexane]-4'-carboxamide 6-oxide, cis-N-[5-(3-fluoromethoxyphenyl)-2-pyrimidinyl]-4'-hydroxy-3-oxospiro[6-azaisobenzofuran-1(3H),1'-cyclohexane]-4'-carboxamide, trans-N-[5-(3-fluoromethoxyphenyl)-2-pyrimidinyl]-3-oxospiro[6-azaisobenzofuran-1(3H),1'-cyclohexane]-4'-carboxamide 6-oxide, cis-N-[5-(3-fluoromethoxyphenyl)-2-pyrimidinyl]-4'-hydroxy-3-oxospiro[6-azaisobenzofuran-1(3H),1'-cyclohexane]-4'-carboxamide 6-oxide, cis-4'-hydroxy-3-oxo-N-(6-phenyl-1,2,4-triazin-3-yl)spiro[6-azaisobenzofuran-1(3H),1'-cyclohexane]-4'-carboxamide, trans-3-oxo-N-(6-phenyl-1,2,4-triazin-3-yl)spiro[6-azaisobenzofuran-1(3H),1'-cyclohexane]-4'-carboxamide 6-oxide, cis-4'-hydroxy-3-oxo-N-(6-phenyl-1,2,4-triazin-3-yl)spiro[6-azaisobenzofuran-1(3H),1'-cyclohexane]-4'-carboxamide 6-oxide, cis-N-[5-(2-difluoromethoxyphenyl)-3-pyrazolyl]-4'-hydroxy-3-oxospiro[6-azaisobenzofuran-1(3H),1'-cyclohexane]-4'-carboxamide, trans-N-[5-(2-difluoromethoxyphenyl)-3-pyrazolyl]-3-oxospiro[6-azaisobenzofuran-1(3H),1'-cyclohexane]-4'-carboxamide 6-oxide, cis-N-[5-(2-difluoromethoxyphenyl)-3-pyrazolyl]-4'-hydroxy-3-oxospiro[6-azaisobenzofuran-1(3H),1'-cyclohexane]-4'-carboxamide 6-oxide, cis-N-[5-(3-difluoromethoxyphenyl)-3-pyrazolyl]-4'-hydroxy-3-oxospiro[6-azaisobenzofuran-1(3H),1'-cyclohexane]-4'-carboxamide, trans-N-[5-(3-difluoromethoxyphenyl)-3-pyrazolyl]-3-oxospiro[6-azaisobenzofuran-1(3H),1'-cyclohexane]-4'-carboxamide 6-oxide, cis-N-[5-(3-difluoromethoxyphenyl)-3-pyrazolyl]-4'-hydroxy-3-oxospiro[6-azaisobenzofuran-1(3H),1'-cyclohexane]-4'-carboxamide 6-oxide, cis-N-[5-(3-fluorophenyl)-3-pyrazolyl]-4'-hydroxy-3-oxospiro[6-azaisobenzofuran-1(3H),1'-cyclohexane]-4'-carboxamide, trans-N-[5-(3-fluorophenyl)-3-pyrazolyl]-3-oxospiro[6-azaisobenzofuran-1(3H),1'-cyclohexane]-4'-carboxamide 6-oxide, cis-N-[5-(3-fluorophenyl)-3-pyrazolyl]-4'-hydroxy-3-oxospiro[6-azaisobenzofuran-1(3H),1'-cyclohexane]-4'-carboxamide 6-oxide, cis-N-[5-(4-fluorophenyl)-3-pyrazolyl]-4'-hydroxy-3-oxospiro[6-azaisobenzofuran-1

(3H),1'-cyclohexane]-4'-carboxamide, trans-N-[5-(4-fluorophenyl)-3-pyrazolyl]-3-oxospiro[6-azaisobenzofuran-1(3H),1'-cyclohexane]-4'-carboxamide 6-oxide, cis-N-[5-(4-fluorophenyl)-3-pyrazolyl]-4'-hydroxy-3-oxospiro[6-azaisobenzofuran-1(3H),1'-cyclohexane]-4'-carboxamide 6-oxide, cis-N-(4-benzoylphenyl)-4'-hydroxy-3-oxospiro[7-azaisobenzofuran-1(3H),1'-cyclohexane]-4'-carboxamide, trans-N-(4-benzoylphenyl)-3-oxospiro[7-azaisobenzofuran-1(3H),1'-cyclohexane]-4'-carboxamide 7-oxide, cis-N-(4-benzoylphenyl)-4'-hydroxy-3-oxospiro[7-azaisobenzofuran-1(3H),1'-cyclohexane]-4'-carboxamide 7-oxide, cis-N-[1-(3,5-difluorophenyl)-4-imidazolyl]-4'-hydroxy-3-oxospiro[7-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide 7-oxide, cis-N-[1-(3,5-difluorophenyl)-4-imidazolyl]-4'-hydroxy-3-oxospiro[7-azaisobenzofuran-1(3H),1'-cyclohexane]-4'-carboxamide 7-oxide, cis-4'-hydroxy-3-oxo-N-[2-phenyl-4-pyridyl]spiro[7-azaisobenzofuran-1(3H),1'-cyclohexane]-4'-carboxamide, trans-3-oxo-N-[2-phenyl-4-pyridyl]spiro[7-azaisobenzofuran-1(3H),1'-cyclohexane]-4'-carboxamide 7-oxide, cis-4'-hydroxy-3-oxo-N-[2-phenyl-4-pyridyl]spiro[7-azaisobenzofuran-1(3H),1'-cyclohexane]-4'-carboxamide 7-oxide, cis-4'-hydroxy-3-oxo-N-(1-phenyl-4-pyrazolyl)spiro[7-azaisobenzofuran-1(3H),1'-cyclohexane]-4'-carboxamide, trans-3-oxo-N-(1-phenyl-4-pyrazolyl)spiro[7-azaisobenzofuran-1(3H),1'-cyclohexane]-4'-carboxamide 7-oxide, cis-4'-hydroxy-3-oxo-N-(1-phenyl-4-pyrazolyl)spiro[7-azaisobenzofuran-1(3H),1'-cyclohexane]-4'-carboxamide 7-oxide, cis-4'-hydroxy-3-oxo-N-(1-phenyl-3-pyrrolyl)spiro[7-azaisobenzofuran-1(3H),1'-cyclohexane]-4'-carboxamide, trans-3-oxo-N-(1-phenyl-3-pyrrolyl)spiro[7-azaisobenzofuran-1(3H),1'-cyclohexane]-4'-carboxamide 7-oxide, cis-4'-hydroxy-3-oxo-N-(1-phenyl-3-pyrrolyl)spiro[7-azaisobenzofuran-1(3H),1'-cyclohexane]-4'-carboxamide 7-oxide, cis-N-[1-(4-fluorophenyl)-3-pyrazolyl]-4'-hydroxy-3-oxospiro[7-azaisobenzofuran-1(3H),1'-cyclohexane]-4'-carboxamide, trans-N-[1-(4-fluorophenyl)-3-pyrazolyl]-3-oxospiro[7-azaisobenzofuran-1(3H),1'-cyclohexane]-4'-carboxamide 7-oxide, cis-N-[1-(4-fluorophenyl)-3-pyrazolyl]-4'-hydroxy-3-oxospiro[7-azaisobenzofuran-1(3H),1'-cyclohexane]-4'-carboxamide 7-oxide, cis-4'-hydroxy-3-oxo-N-(1-phenyl-3-pyrazolyl)spiro[4-azaisobenzofuran-1(3H),1'-cyclohexane]-4'-carboxamide, trans-3-oxo-N-(1-phenyl-3-pyrazolyl)spiro[4-azaisobenzofuran-1(3H),1'-cyclohexane]-4'-carboxamide 4-oxide, cis-4'-hydroxy-3-oxo-N-(1-phenyl-3-pyrazolyl)spiro[4-azaisobenzofuran-1(3H),1'-cyclohexane]-4'-carboxamide 4-oxide, cis-4'-hydroxy-3-oxo-N-(1-phenyl-4-pyrazolyl)spiro[4-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide 4-oxide, cis-4'-hydroxy-3-oxo-N-(1-phenyl-4-pyrazolyl)spiro[4-azaisobenzofuran-1(3H),1'-cyclohexane]-4'-carboxamide 4-oxide, cis-N-[1-(3-fluorophenyl)-4-pyrazolyl]-4'-hydroxy-3-oxospiro[4-azaisobenzofuran-1(3H),1'-cyclohexane]-4'-carboxamide, trans-N-[1-(3-fluorophenyl)-4-pyrazolyl]-3-oxospiro[4-azaisobenzofuran-1(3H),1'-cyclohexane]-4'-carboxamide 4-oxide, cis-N-[1-(3-fluorophenyl)-4-pyrazolyl]-4'-hydroxy-3-oxospiro[4-azaisobenzofuran-1(3H),1'-cyclohexane]-4'-carboxamide 4-oxide, cis-4'-hydroxy-3-oxo-N-(1-phenyl-3-pyrazolyl)spiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide 6-oxide, cis-4'-hydroxy-3-oxo-N-(1-phenyl-3-pyrazolyl)spiro[6-azaisobenzofuran-1(3H),1'-cyclohexane]-4'-carboxamide 6-oxide, cis-N-[1-(4-fluorophenyl)-3-pyrazolyl]-4'-hydroxy-3-oxospiro[6-azaisobenzofuran-1(3H),1'-cyclohexane]-4'-carboxamide, trans-N-[1-(4-fluorophenyl)-3-pyrazolyl]-3-oxospiro[6-azaisobenzofuran-1(3H),1'-cyclohexane]-4'-carboxamide 6-oxide, cis-N-[1-(4-fluorophenyl)-3-pyrazolyl]-4'-hydroxy-3-oxospiro[6-azaisobenzofuran-1(3H),1'-cyclohexane]-4'-carboxamide 6-oxide, cis-N-[1-(2-fluorophenyl)-3-pyrazolyl]-4'-hydroxy-3-oxospiro[6-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide 6-oxide, cis-N-[1-(2-fluoro-4-hydroxyphenyl)-3-pyrazolyl]-4'-hydroxy-3-oxospiro[6-azaisobenzofuran-1(3H),1'-cyclohexane]-4'-carboxamide, trans-N-[1-(2-fluoro-4-hydroxyphenyl)-3-pyrazolyl]-3-oxospiro[6-azaisobenzofuran-1(3H),1'-cyclohexane]-4'-carboxamide 6-oxide, cis-N-[1-(2-fluorophenyl)-3-pyrazolyl]-4'-hydroxy-3-oxospiro[6-azaisobenzofuran-1(3H),1'-cyclohexane]-4'-carboxamide 6-oxide, cis-N-[1-(2-fluoro-4-hydroxyphenyl)-3-pyrazolyl]-4'-hydroxy-3-oxospiro[6-azaisobenzofuran-1(3H),1'-cyclohexane]-4'-carboxamide 6-oxide, cis-4'-hydroxy-3-oxo-N-(5-phenyl-1,2,4-thiadiazol-3-yl)spiro[6-azaisobenzofuran-1(3H),1'-cyclohexane]-4'-carboxamide, trans-3-oxo-N-(5-phenyl-1,2,4-thiadiazol-3-yl)spiro[6-azaisobenzofuran-1(3H),1'-cyclohexane]-4'-carboxamide 6-oxide, cis-4'-hydroxy-3-oxo-N-(5-phenyl-1,2,4-thiadiazol-3-yl)spiro[6-azaisobenzofuran-1(3H),1'-cyclohexane]-4'-carboxamide 6-oxide, cis-4'-hydroxy-3-oxo-N-(5-phenyl-3-isoxazolyl)spiro[6-azaisobenzofuran-1(3H),1'-cyclohexane]-4'-carboxamide, trans-3-oxo-N-(5-phenyl-3-isoxazolyl)spiro[6-azaisobenzofuran-1(3H),1'-cyclohexane]-4'-carboxamide 6-oxide, cis-4'-hydroxy-3-oxo-N-(5-phenyl-3-isoxazolyl)spiro[6-azaisobenzofuran-1(3H),1'-cyclohexane]-4'-carboxamide 6-oxide, cis-4'-hydroxy-3-oxo-N-(6-phenyl-3-pyridyl)spiro[6-azaisobenzofuran-1(3H),1'-cyclohexane]-4'-carboxamide, trans-3-oxo-N-(6-phenyl-3-pyridyl)spiro[6-azaisobenzofuran-1(3H),1'-cyclohexane]-4'-carboxamide 6-oxide, cis-4'-hydroxy-3-oxo-N-(6-phenyl-3-pyridyl)spiro[6-azaisobenzofuran-1(3H),1'-cyclohexane]-4'-carboxamide 6-oxide, cis-4'-hydroxy-3-oxo-N-(2-phenyl-3-thiazolyl)spiro[6-azaisobenzofuran-1(3H),1'-cyclohexane]-4'-carboxamide, trans-3-oxo-N-(2-phenyl-3-thiazolyl)spiro[6-azaisobenzofuran-1(3H),1'-cyclohexane]-4'-carboxamide 6-oxide, cis-4'-hydroxy-3-oxo-N-(2-phenyl-3-thiazolyl)spiro[6-azaisobenzofuran-1(3H),1'-cyclohexane]-4'-carboxamide 6-oxide, cis-4'-hydroxy-3-oxo-N-(2-phenyl-1,2,3-triazol-4-yl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide 6-oxide, cis-4'-hydroxy-3-oxo-N-(2-phenyl-1,2,3-triazol-4-yl)spiro[6-azaisobenzofuran-1(3H),1'-cyclohexane]-4'-carboxamide 6-oxide, trans-N-[1-(4-fluorophenyl)-4-hydroxy-3-pyrazolyl]-3-oxospiro[7-azaisobenzofuran-1(3H),1'-cyclohexane]-4'-carboxamide, trans-3-oxo-N-(4-hydroxy-1-phenyl-3-pyrazolyl)spiro[4-azaisobenzofuran-1(3H),1'-cyclohexane]-4'-carboxamide, trans-3-oxo-N-(4-hydroxy-1-phenyl-3-pyrazolyl)spiro[6-azaisobenzofuran-1(3H),1'-cyclohexane]-4'-carboxamide, trans-N-[1-(4-fluorophenyl)-4-hydroxy-3-pyrazolyl]-3-oxospiro[6-azaisobenzofuran-1(3H),1'-cyclohexane]-4'-carboxamide or trans-N-[1-(2-fluorophenyl)-4-hydroxy-3-pyrazolyl]-3-oxospiro[6-azaisobenzofuran-1(3H),1'-cyclohexane]-4'-carboxamide.

The specific compound represented by the general formula (I) is also, for example, trans-N-[5-(4-hydroxyphenyl)-2-pyrazinyl]-3'-oxospiro[cyclohexane-1,1'(3'H)-isobenzofuran]-4-carboxamide, trans-N-[1-(4-hydroxyphenyl)-4-imidazolyl]-3'-oxospiro[cyclohexane-1,1'(3'H)-isobenzofuran]-4-carboxamide, trans-N-[5-(4-hydroxyphenyl)-2-pyrimidinyl]-3'-oxospiro[cyclohexane-1,1'(3'H)-isobenzofuran]-4-carboxamide, trans-N-[1-(2-fluoro-4-hydroxyphenyl)-3-pyrazolyl]-3-oxospiro[6- azaisobenzofuran-1(3H),1'-cyclohexane]-4'-carboxamide, trans-N-[1-(2-fluoro-3,4-dihydroxyphenyl)-3-pyrazolyl]-3-oxospiro[6-azaisobenzofuran-1(3H),1'-cyclohexane]-4'-carboxamide, trans-N-[1-(2-fluoro-4,5-dihydroxyphenyl)-3-pyrazolyl]-3-oxospiro[6-azaisobenzofuran-1(3H),1'-cyclohexane]-4'-carboxamide or trans-N-[1-(2-fluoro-4,6-dihydroxyphenyl)-3-pyrazolyl]-3-oxospiro[6-azaisobenzofuran-1(3H),1'-cyclohexane]-4'-carboxamide.

The process for producing compounds of this invention is illustrated as follows.

Compounds of this invention (I) can be synthesized, for example, by the following processes for production or the processes shown in examples, but these embodiments are not intended to restrict the process for producing compounds of this invention (I).

Production Process 1

A compound of the general formula (II):

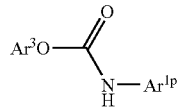

(II)

wherein $Ar^{1p}$ represents aryl or heteroaryl which may be substituted, the substituent being selected from the group consisting of halogen, nitro, lower alkyl, halo(lower)alkyl, cyclo(lower)alkyl, lower alkenyl, lower alkoxy, halo(lower)alkoxy, lower alkylthio, lower alkanoyl, lower alkoxycarbonyl, a group of formula: $-Q^p-Ar^{2p}$, and an optionally protected, hydroxy, lower alkylene optionally substituted with oxo, hydroxy(lower)alkyl or carboxyl group;

$Ar^{2p}$ represents aryl or heteroaryl which may be substituted, the substituent being selected from the group consisting of halogen, cyano, lower alkyl, halo(lower)alkyl, lower alkoxy, halo(lower)alkoxy, di-lower alkylamino, lower alkanoyl, aryl, and an optionally protected hydroxy(lower)alkyl, hydroxy or lower alkyl amino group;

$Ar^3$ represents phenyl which may be substituted by halogen or nitro;

$Q^p$ represents a single bond or optionally protected carbonyl; is reacted with a compound of the general formula (III):

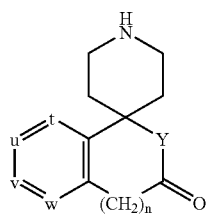

(III)

wherein n, t, u, v, w and Y have the same meanings as mentioned above;

to provide a compound of the general formula (IV-1):

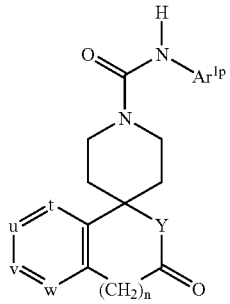

(IV-1)

wherein $Ar^{1p}$, n, t, u, v, w and Y have the same meanings as mentioned above;

optionally followed by elimination of a protective group and/or oxidation of a nitrogen atom to give a compound of the general formula (I-1):

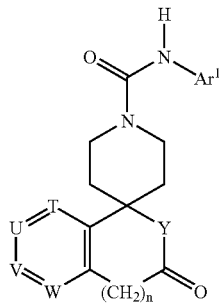

(I-1)

wherein $Ar^1$, n, T, U, V, W and Y have the same meanings as mentioned above; and an N-oxide derivative thereof.

This production process refers to the process for producing a compound of the general formula (I), wherein X is nitrogen, that is, a compound of the general formula (I -1).

When a reactant has an amino, hydroxy, carboxyl, oxo, carbonyl, or the like group which does not participate in the reaction, the reaction may be carried out after protecting the amino, hydroxy, carboxyl, oxo, carbonyl, or the like group with an amino protecting group, hydroxy protecting group, carboxyl protecting group, or oxo- or carbonyl-protecting group, followed by deprotection after completion of the reaction.

"Amino protecting group" includes aralkyl (for example benzyl, p-methoxybenzyl, 3,4-dimethoxybenzyl, o-nitrobenzyl, p-nitrobenzyl, benzhydryl, trityl); lower alkanoyl (for example formyl, acetyl, propionyl, butyryl, pivaloyl); benzoyl; arylalkanoyl (for example phenylacetyl, phenoxyacetyl); lower alkoxycarbonyl (for example methoxycarbonyl, ethoxycarbonyl, propyloxycarbonyl, tert-butoxycarbonyl); aralkyloxycarbonyl (for example benzyloxycarbonyl, p-nitrobenzyloxycarbonyl, phenethyloxycarbonyl); lower alkylsilyl (for example trimethylsilyl, tert-butyldimethylsilyl); and the like, especially acetyl, pivaloyl, benzoyl, ethoxycarbonyl, tert-butoxycarbonyl, and the like.

"Hydroxy protecting group" includes lower alkyl (for example methyl, ethyl, propyl, isopropyl, tert-butyl); lower alkylsilyl (for example trimethylsilyl, tert-butyldimethylsilyl); lower alkoxymethyl (for example methoxymethyl, 2-methoxyethoxymethyl); tetrahydropyranyl; trimethylsilylethoxymethyl; aralkyl (for example benzyl, p-methoxybenzyl, 2,3-dimethoxybenzyl, o-nitrobenzyl, p-nitrobenzyl, trityl); acyl (for example formyl, acetyl), and the like, especially methyl, methoxymethyl, tetrahydropyranyl, trityl, trimethylsilylethoxymethyl, tert-butyldimethylsilyl, acetyl, and the like.

"Carboxyl protecting group" includes lower alkyl (for example methyl, ethyl, propyl, isopropyl, tert-butyl); lower haloalkyl (for example 2,2,2-trichloroethyl); lower alkenyl (for example 2-propenyl); aralkyl (for example benzyl, p-methoxybenzyl, p-nitrobenzyl, benzhydryl, trityl); and the like, especially methyl, ethyl, tert-butyl, 2-propenyl, benzyl, p-methoxybenzyl, benzhydryl, and the like.

"Oxo- or carbonyl-protecting group" includes acetal or ketal (for example ethylene ketal, trimethylene ketal, dimethyl ketal), and the like.

The reaction between a compound of the general formula (II) and a compound of the general formula (III) is usually carried out by employing an equivalent to excessive mole, preferably an equivalent to 1.5 moles of compound (III) based on 1 mole of compound (II).

The reaction is usually carried out in an inert solvent, and as the inert solvent, made is use of, for example, methylene chloride, chloroform, tetrahydrofuran, dimethylformamide, dimethyl sulfoxide or the mixture, and the like, preferably.

The aforesaid reaction may be preferably carried out in the presence of base, including organic bases (for example triethylamine, diisopropylethylamine, pyridine, 4-dimethylaminopyridine) or inorganic bases (for example sodium hydroxide, potassium hydroxide), and the like.

The amount of the aforesaid base employed is usually an equivalent to excessive mole, preferably 1 to 5 moles based on 1 mole of a compound of the general formula (II).

Reaction temperature is usually −30° C. to 200° C., preferably 20° C. to 100° C.

Reaction time is usually 5 minutes to 7 days, preferably 30 minutes to 24 hours.

At the conclusion of the reaction, the crude product of a compound of the general formula (IV-1) can be obtained by usual treatment. Thus obtained compound (IV-1) is purified by the conventional method, or not purified, if necessary followed by optional combination of elimination reaction of amino-, hydroxy-, carboxyl-, oxo- and carbonyl-protecting group to give a compound of the general formula (I-1).

The elimination of protecting groups may be carried out depending upon the kinds of the aforesaid protecting groups, the stability of a desired compound (I-1) and so on, for example, by the manner described in the literature [Protective Groups in Organic Synthesis, T. W. Greene, John Wiley & Sons, (1981)] or its similar manner, for example, solvolysis using acid or base, that is, for example 0.01 mole to a large excess of acid, preferably trifluoroacetic acid, formic acid, hydrochloric acid, or the like, or an equivalent mole to a large excess of base, preferably potassium hydroxide, calcium hydroxide, or the like; chemical reduction using metallic complex hydride, or the like; or catalytic reduction using palladium-carbon catalyst, Raney nickel catalyst, or the like.

The oxidation of a nitrogen atom may be carried out by using of an oxydizingagent (for example m-chloroperbenzoic acid, dioxirane, sodium periodate and hydrogen peroxide). Reaction between a compound of the general formula (IV-1) and an oxydizing agent is usually carried out by employing 0.5 mole to excessive moles, preferably 1 mole to 5 moles of the oxydizing agent based on 1 mole of compound (IV-1).

The reaction is usually carried out in an appropriate solvent which depend on the oxydizing agent used in the reaction. Preferable examples of the solvent include methylene chloride and chloroform for m-chloroperbenzoic acid, acetone and water for dioxirane.

Reaction temperature is usually −50° C. to 100° C., preferably −20° C. to 50° C.

Reaction time is usually 15 minutes to 7 days, preferably 30 minutes to 24 hours.

Production Process 2

A compound of the general formula (V):

wherein $Ar^{1p}$ has the same meaning as mentioned above; is reacted with a carboxylic acid of the general formula (VI):

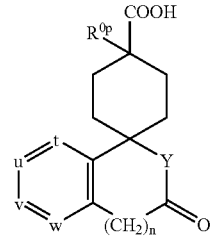

wherein n, $R^{0p}$, t, u, v, w and Y have the same meanings as mentioned above;

or its reactive derivative to provide a compound of the general formula (IV-2):

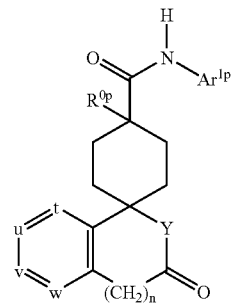

wherein $Ar^{1p}$, n, $R^{0p}$, t, u, v, w and Y have the same meanings as mentioned above;

optionally followed by elimination of a protecting group and/or oxidation of a nitrogen atom to give a compound of the general formula (I-2):

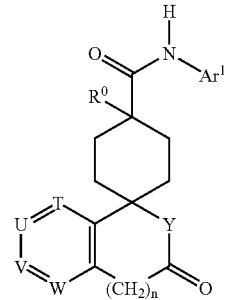

wherein $Ar^1$, n, $R^0$, T, U, V, W and Y have the same meanings as mentioned above; and an N-oxide derivative thereof.

This production process refers to the process for producing compounds of the general formula (I), wherein X is methine, that is, a compound of the general formula (I-2).

Reaction between a compound of the general formula (V) and a carboxylic acid of the general formula (VI) is usually carried out by employing 0.5 mole to excessive moles, preferably 1 mole to 1.5 mole of carboxylic acid (VI) based on 1 mole of compound (V).

The reaction is usually carried out in an inert solvent, and preferable examples of the inert solvent include methylene chloride, chloroform, tetrahydrofuran, dimethylformamide, pyridine or a mixture thereof, and the like.

The aforesaid reaction is preferably carried out in the presence of condensing agents, for example N, N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yl-oxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoryl azide, 1,1'-carbonyldiimidazole, or the like.

The aforesaid condensing agent is usually employed at 1 mole to excessive mole, preferably 1 mole to 1.5 moles based on 1 mole of compound (VI).

Reaction temperature is usually −50° C. to 100° C., preferably −20° C. to 50° C.

Reaction time is usually 30 minutes to 7 days, preferably 1 hour to 24 hours.

A compound of formula (I-2) is also produced by reacting a compound of the general formula (V) with a reactive derivative of the carboxylic acid (VI) instead of the carboxylic acid (VI).

The reactive derivatives of carboxylic acid of the general formula (VI) include acid halides, mixed acid anhydrides, activated esters, activated amides, and the like.

The acid halides of carboxylic acid of the general formula (VI) may be obtained by reacting a carboxylic acid of the general formula (VI) with a halogenating agent according to the conventional method. Halogenating agent includes thionyl chloride, phosphorus trichloride, phosphorus pentachloride, phosphorus oxychloride, phosphorus tribromide, oxalyl chloride, phosgene, and the like.

The mixed acid anhydrides of carboxylic acid of the general formula (VI) may be obtained by reacting a carboxylic acid of the general formula (VI) with alkyl chlorocarbonate (for example ethyl chlorocarbonate); aliphatic carboxylic acid chloride (for example pivaloyl chloride), and the like according to the conventional method.

The activated esters of carboxylic acid of the general formula (VI) may be obtained by reacting a carboxylic acid of the general formula (VI) with N-hydroxy compound (for example N-hydroxysuccinimide, N-hydroxyphthalimide, 1-hydroxybenzotriazole); phenol compound (for example 4-nitrophenol, 2,4-dinitrophenol, 2,4,5-trichlorophenol, pentachlorophenol), or the like in the presence of a condensing agent (for example N,N'-dicyclohexylcarbodiimide, 1-(3-dimethylaminopropyl)-3-ethylcarbodiimide) according to the conventional method.

The activated amides of carboxylic acid of the general formula (VI) may be obtained by reacting a carboxylic acid of the general formula (VI) with for example 1,1'-carbonyldiimidazole, 1,1'-carbonylbis(2-methylimidazole), or the like according to the conventional method.

Reaction between a compound of the general formula (V) and a reactive derivative of the carboxylic acid of the general formula (VI) is usually carried out by employing 0.5 mole to excessive mole, preferably 1 mole to 1.5 moles of the reactive derivative of carboxylic acid (VI) based on 1 mole of compound (V).

The reaction is usually carried out in an inert solvent, and preferable examples of the inert solvent include methylene chloride, chloroform, tetrahydrofuran, dimethylformamide, pyridine or a mixture thereof, and the like.

The aforesaid reaction proceeds in the absence of bases, but it is preferable to carry out the reaction in the presence of bases to promote the reaction smoothly.

The aforesaid bases include organic bases (for example triethylamine, diisopropylethylamine, pyridine, 4-dimethylaminopyridine) or inorganic bases (for example sodium hydroxide, potassium hydroxide, sodium carbonate, potassium carbonate, sodium hydrogen carbonate), and the like.

It is preferable to employ 1 mole to excessive mole of the aforesaid base to 1 mole of a compound of the general formula (V). When the aforesaid base is liquid, the aforesaid base can also be used as a solvent.

Reaction temperature is usually −50° C. to 100° C., preferably −20° C. to 50° C.

Reaction time is usually 5 minutes to 7 days, preferably 30 minutes to 24 hours.

A compound of the general formula (I-2) can be produced by treating a reaction mixture in the usual way after deprotection if the product has a protecting group at the conclusion of the reaction, or by treating the mixture directly in the usual way if the protective group is absent.

Elimination of the protecting groups, oxidation of the nitrogen atom and post-treatment, and the like can be carried out according to the method described in the aforesaid production process 1.

Compounds of the general formula (I-1) or (I-2) may readily be isolated and purified by the conventional separation technique, for example, solvent extraction, recrystallization, column chromatography, preparative thin layer chromatography, or/and the like.

These compounds may be converted into the pharmaceutically acceptable salts or esters by the conventional method, on the contrary, the conversion of the salts or esters into free compounds may also be carried out according to the conventional method.

Compounds of the general formula (II), (III), (V) or (VI) are commercially available, or are prepared according to the methods described in the literature [Japanese Patent Unexamined Publication No.94/263737-A, U.S. Pat. No. 3,301,857, J. Org. Chem, 40: 1427 (1975), International Patent Publication WO95/28389 or the like], or analogous methods thereto or the methods shown below or in Examples, optionally in combination.

Production Process A

(V)

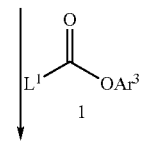

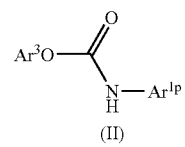

(II)

wherein $L^1$ represents halogen; $Ar^{1p}$ and $Ar^3$ have the same meanings as given above;

This process refers to a process for producing a compound of the general formula (II). Compound (II) is prepared by reacting a compound of the general formula (V) with a compound of the general formula 1 according to this process.

The reaction between a compound (V) and a compound 1 is usually carried out by employing 0.5 mole to excessive mole, preferably an equivalent to 1.5 moles of compound 1 based on 1 mole of compound (V).

The reaction is usually carried out in an inert solvent, and the preferable examples of the inert solvent include methylene chloride, chloroform, tetrahydrofuran, ethyl ether, benzene, toluene, dimethylformamide or a mixture thereof, and the like.

It is preferable to carry out the reaction in the presence of bases. The aforesaid bases include organic bases (for example triethylamine, diisopropylethylamine, pyridine, 4-dimethylaminopyridine) or inorganic bases (for example sodium hydroxide, potassium hydroxide, sodium carbonate, potassium carbonate, sodium hydrogen carbonate), and the like.

It is preferable to employ an equivalent to excessive mole of the aforesaid base to 1 mole of a compound (V). When the aforesaid base is liquid, the aforesaid base can be used also as a solvent.

Reaction temperature is usually −78° C. to 100° C., preferably −20° C. to 50° C.

Reaction time is usually 5 minutes to 7 days, preferably 30 minutes to 24 hours.

Compounds of formula 1 are commercially available, or are prepared according to the conventional method, the methods described in Examples, or the like methods, optionally in combination.

Production Process B

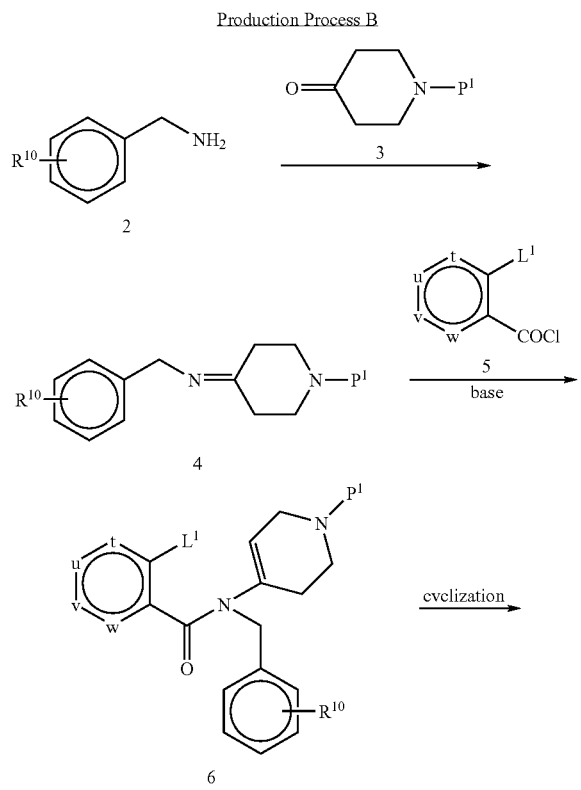

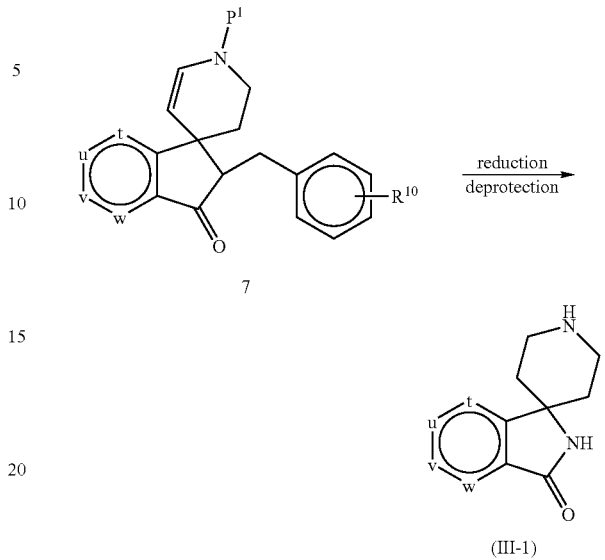

wherein $P^1$ represents an amino protecting group; $R^{10}$ represents hydrogen, nitro, lower alkyl or lower alkoxy; $L^1$, t, u, v and w have the same meanings as given above.

This process refers to a process for producing compounds of the general formula (III-1). Compound (III-1) may so be prepared by the present process that a compound of the general formula 2 is subjected to dehydrogenated condensation with a compound of the general formula 3 to give a compound of the general formula 4, which is subjected to reaction with a compound of the general formula 5 in the presence of a base to yield a compound of the general formula 6 and then the compound 6 is cyclized by an intra-molecular Heck reaction to give a compound of the general formula 7, and then the compound 7 is subjected to reduction, optionally followed by elimination of amino protecting group $P^1$.

Amino protecting group $P^1$ includes the amino protecting groups described in the aforesaid production process 1.

A step for preparing compound 4 by dehydrogenated condensation of compound 2 with compound 3 is usually carried out in an inert solvent, for example benzene, toluene, or the like.

Reaction temperature is preferably from room temperature to the boiling point of a solvent used and reaction time is preferably from 30 minutes to 24 hours.

A step for preparing compound 6 from compound 4 is usually carried out in an inert solvent (for example benzene, toluene, methylene chloride, chloroform, acetonitrile, dimethylformamide) in the presence of base (for example triethylamine, diisopropylethylamine, pyridine, 4-dimethylaminopyridine).

Reaction temperature is preferably from 0° C. to the boiling point of a solvent used and reaction time is preferably from 30 minutes to 24 hours.

So-called intramolecular Heck reaction well known in the field of organic chemistry can be applied to the step for preparing compound 7 from compound 6.

The aforesaid step is usually carried out in an inert solvent (for example benzene, toluene, tetrahydrofuran, acetonitrile, dimethylformamide, N-methylpyrrolidone) in the presence of palladium catalyst (for example palladium acetate, palladium chloride), phosphine ligand (for example triphenylphosphine, tri-2-furylphosphine) and base (for example potassium carbonate, triethylamine), optionally additives (for example tetraethylammonium chloride).

Reaction temperature is preferably from room temperature to the boiling point of a solvent used in reaction and reaction time is preferably from 30 minutes to 24 hours.

As a method for reduction in the step for preparing compound (III-1) from compound 7, for example catalytic reduction is preferable.

The catalytic reduction is usually carried out in an inert solvent (for example methanol, ethanol, methylene chloride, chloroform, tetrahydrofuran, dimethylformamide, acetic acid) in the presence of a catalyst such as palladium-carbon at 1 to 50 atmospheric pressure of hydrogen.

Reaction temperature is preferably from room temperature to the boiling point of a solvent used and reaction time is preferably from 30 minutes to 24 hours.

At the conclusion of the reaction, if a reaction product has a protecting group, compound (III-1) can be prepared by elimination of the protecting group.

Elimination of a protecting group can be carried out according to the method described in the aforesaid production process 1.

This step may also be carried out by elimination of the protecting group of compound 7, followed by reduction of the resulting compound.

Compounds of the general formula 2, 3 or 5 are commercially available, or may be prepared according to the conventional method, the methods shown in Examples, or the like methods, optionally in combination.

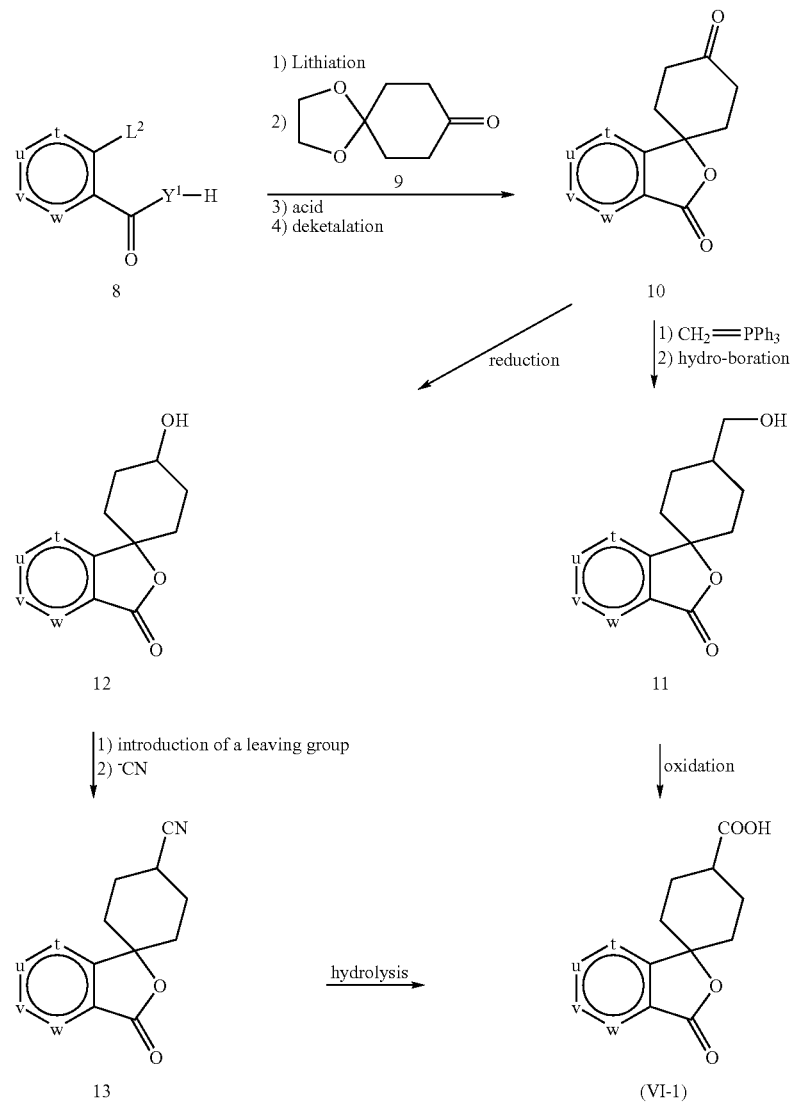

Production Process C wherein L² represents hydrogen or halogen;
Ph represents phenyl;
Y¹ represents oxygen or imino substituted with lower alkyl or aryl;
t, u, v and w have the same meanings as given above.

This production process refers to the process for preparing compound of the general formula (VI-1). The compound represented by the general formula of (VI-1) is novel compound, which is not disclosed in the literature. The compound can be produced according to the present production process, that is, a compound of the general formula 8 is subjected to lithiation, reaction with compound 9 and lactonization with an acid, followed by deketalation to yield a compound of the general formula 10; and 1) methylene group is introduced to the compound 10, which is followed by hydroboration to give a compound of the general formula 11, and the compound is subjected to oxidation reaction, or 2) the compound 10 is reduced to give a compound of the general formula 12, which is subjected to introduction of a leaving group and then cyanization to give a compound of the general formula 13, followed by hydrolysis of the compound 13 at the cyano group.

Lithiation in the step preparing compound 10 from compound 8 is usually carried out by allowing compound 8 to be acted on by an organic lithium reagent (for example n-butyllithium, lithium 2,2,6,6-tetramethyl-piperidide) in an inert solvent (for example tetrahydrofuran, diethyl ether).

Reaction temperature is usually from −120° C. to 0° C., preferably from −100° C. to −50° C. and reaction time is preferably from 1 hour to 4 hours.

Reaction between the resulting lithio type and a ketone of the general formula 9 is usually carried out in an inert solvent (for example tetrahydrofuran, diethyl ether).

Reaction temperature is preferably from −100° C. to room temperature and reaction time is preferably from 10 minutes to 2 hours.

The resulting compound can be lactonized by treating with an acid (for example hydrochloric acid, sulfuric acid).

Reaction temperature is preferably from 0° C. to the boiling point of a solvent used and reaction time is preferably from 30 minutes to 8 hours.

Compound 10 can be prepared by subjecting the resulting lactone type to deketalation according to the conventional method.

Reaction temperature is preferably from 50° C. to the boiling point of a solvent used and reaction time is preferably from 1 hour to 24 hours.

The method used for converting oxo group to hydroxymethyl group, which is well known in the field of organic chemistry, can be applied to the step for preparing compound 11 from compound 10 and the step is usually carried out by reacting compound 10 with for example methylenetriphenylphosphorane to introduce a methylene group, followed by hydroboration in an inert solvent (for example benzene, toluene, methylene chloride, chloroform, acetonitrile, tetrahydrofuran, dimethylformamide).

In both steps for introducing methylene group and for hydroboration, reaction temperature is preferably from 0° C. to the boiling point of a solvent used and reaction time is preferably from 30 minutes to 8 hours.

The method used for oxidizing hydroxymethyl group to carboxyl group, which is well known in the field of organic chemistry, can be applied to the step for preparing compound (VI-1) from compound 11 and the step is usually carried out by using an oxidizing agent such as sodium periodate and a catalytic amount of ruthenium chloride, in an inert solvent (for example benzene, toluene, methylene chloride, chloroform, acetonitrile, dimethylformamide).

Reaction temperature is preferably from 0° C. to the boiling point of a solvent used and reaction time is preferably from 30 minutes to 8 hours.

The method used for reducing oxo group to hydroxyl group, which is well known in the field of organic chemistry, can be applied to the step for preparing compound 12 from compound 10 and the step is usually carried out by using a reducing agent (for example sodium borohydride, lithium borohydride), in an inert solvent (for example water, methanol, ethanol, tetrahydrofuran or a mixture thereof).

Reaction temperature is preferably from −20° C. to 50° C. and reaction time is preferably from 10 minutes to 4 hours.

The method used for converting hydroxy group to cyano group, which is well known in the field of organic chemistry, can be applied to the step for preparing compound 13 from compound 12 and the step is usually carried out by reacting compound 12 with for example methanesulfonyl chloride, p-toluenesulfonyl chloride, or the like to convert hydroxy group to a leaving group in the presence of base (for example triethylamine, pyridine), followed by reacting the resulting compound with a cyanide (for example sodium cyanide, potassium cyanide, tetraethylammonium cyanide, tetrabutylammonium cyanide).

The step for converting hydroxy group to a leaving group is usually carried out in an inert solvent (for example methylene chloride, chloroform, ethyl acetate, acetonitrile, tetrahydrofuran, dimethylformamide). Reaction temperature is preferably from −20° C. to room temperature and reaction time is preferably from 10 minutes to 8 hours.

The step for reacting with a cyanide is usually carried out in an inert solvent (for example tetrahydrofuran, dioxane, dimethylformamide, N-methylpyrrolidone, dimethyl sulfoxide). Reaction temperature is preferably from 50° C. to 120° C. and reaction time is preferably from 2 to 24 hours.

Hydrolysis of cyano group, which is well known in the field of organic chemistry, can be applied to the step for preparing compound (VI-1) by hydrolysis of the cyano group of compound 13 and the step is usually carried out by using an acid (for example hydrochloric acid, sulfuric acid) or a base (for example sodium hydroxide, potassium hydroxide, calcium hydroxide), in a solvent (for example methanol, ethanol, tetrahydrofuran, dioxane, water or a mixture thereof).

Reaction temperature is preferably from 50° C. to the boiling point of a solvent used and reaction time is preferably from 1 to 48 hours.

Compounds of the general formula (VI-1) have two kinds of stereoisomers represented by the general formula (VI-1-a) or (VI-1-b):

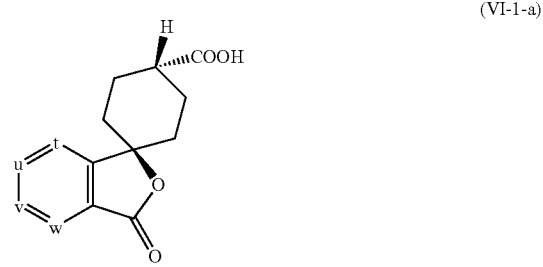

-continued

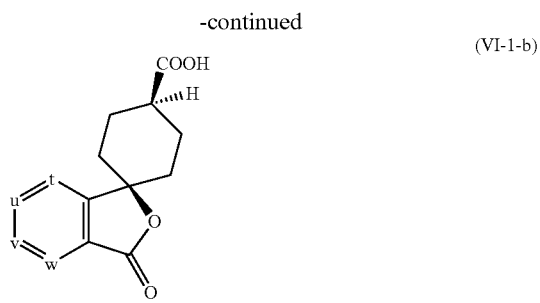

(VI-1-b)

wherein t, u, v and w have the same meanings as given above.

These stereoisomers can be separated from the mixture by the conventional method such as chromatography, fractional recrystallization, and the like.

Compounds of the general formula (VI-1-a) or (VI-1-b) can be prepared by using an intermediate product which is obtained by separation of the stereoisomers of the general compound 11, 12 or 13.

Compounds of the general formula 8 or 9 are commercially available, or are prepared according to the conventional method, the methods described in Examples, or the like methods, optionally in combination.

Production Process D

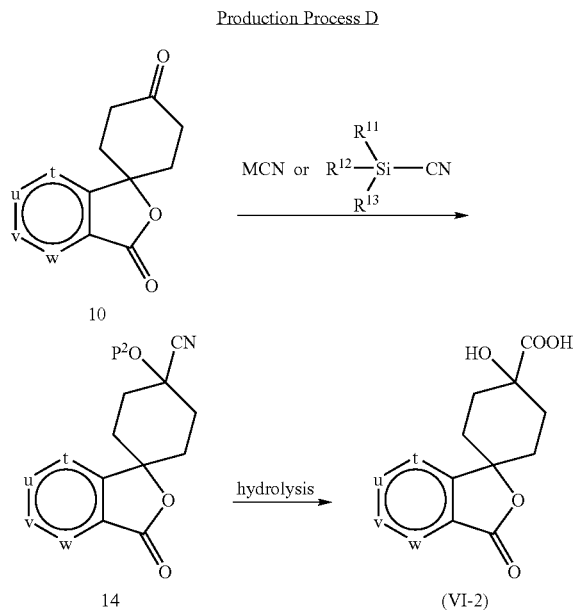

wherein MCN represents sodium cyanide, potassium cyanide or the like; $R^{11}$, $R^{12}$ and $R^{13}$ each independently represent lower alkyl group; $P^2$ represents hydrogen or a group represented by the formula $R^{11}R^{12}R^{13}Si$; t, u, v and w have the same meanings as given above.

This production process refers to the process for preparing compound of the general formula (VI-2). The compound can be produced according to the present production process, that is, a compound of the general formula 10 is derived to a cyanohydrin or a trialkylsilyl ether of cyanohydrin 14, followed by hydrolysis to yield a compound of the general formula (VI-2).

The method used for converting a ketone to a cyanohydrin, which is well known in the field of organic chemistry, can be applied to the step for preparing compound 14 from compound 10 and the step is usually carried out by reacting compound 10 with for example sodium cyanide, potassium cyanide, or the like to convert the ketone to the cyanohydrin.

The reaction is usually carried out in an inert solvent (for example methanol, and ethanol). Reaction temperature is preferably from 0° C. to 100° C. and reaction time is preferably from 30 minutes to 24 hours.

The method used for converting a ketone to a trialkylsilyl ether of cyanohydrin, which is well known in the field of organic chemistry, can be applied to the step for preparing compound 14 from compound 10 and the step is usually carried out by reacting compound 10 with for example trimethylsilyl cyanide, tert-butyldimethylsilyl cyanide, or the like to convert the ketone to the trialkylsilyl ethere of the cyanohydrin.

The reaction is usually carried out in an inert solvent (for example tetrahydrofurane and dichloromethane). Reaction temperature is preferably from 0° C. to 100° C. and reaction time is preferably from 30 minutes to 24 hours.

The aforesaid reaction may be preferably carried out in the presence of base (for example triethylamine and the like) or Lewis acid (for example zinc iodide and the like).

Hydrolysis of cyano group, which is well known in the field of organic chemistry, can be applied to the step for preparing compound (VI-2) by hydrolysis of the cyano group of compound 14 and the step is usually carried out by using an acid (for example hydrochloric acid, sulfuric acid) or a base (for example sodium hydroxide, potassium hydroxide, calcium hydroxide), in a solvent (for example methanol, ethanol, tetrahydrofuran, dioxane, water or a mixture thereof).

Reaction temperature is preferably from 50° C. to the boiling point of a solvent used and reaction time is preferably from 1 to 48 hours.

Compounds of the general formula (VI-2) have two kinds of stereoisomers represented by the general formula (VI-2-a) or (VI-2-b):

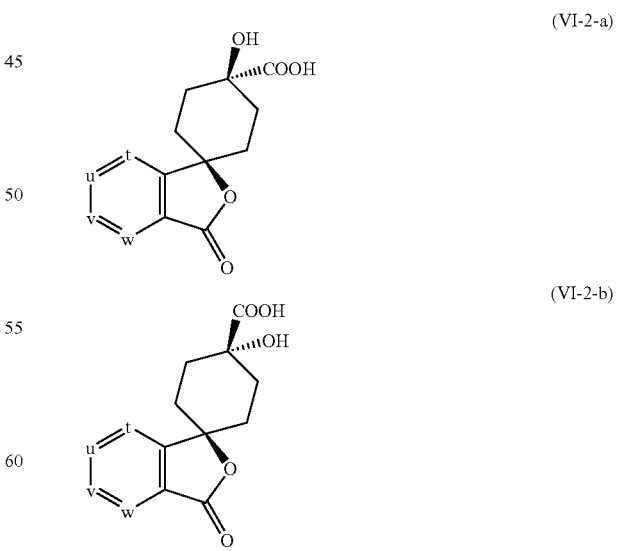

wherein t, u, v and w have the same meanings as given above.

These stereoisomers can be separated from the mixture by the conventional method such as chromatography, fractional recrystallization, and the like.

Compounds of the general formula (VI-2-a) or (VI-2-b) can be prepared by using an intermediate product which is obtained by separation of the stereoisomers of the general compound 14.

The utility of compounds of the present invention as a medicament is proved by describing NPY antagonistic activity, for example, in the following pharmacological tests.

Pharmacological Test 1 (NPY Binding Inhibition Test)

cDNA sequence encoding human NPY Y5 receptor [International patent publication number WO96/16542] was cloned into expression vectors pcDNA3, pRc/RSV (made by Invitrogen Inc.) and pCI-neo (made by Promega Inc.). This obtained expression vectors were transfected to host cells COS-7, CHO and LM(tk-) (American Type Culture Collection) by cationic lipid method [Proceedings of the National Academy of Sciences of the United States of America, 84: 7413(1987)] to give NPY Y5 receptor expression cells.

A membrane sample prepared from the cells which expressed NPY Y5 receptor was incubated together with a test compound and [$^{125}$I]peptideYY (NEN) (20,000 cpm) in an assay buffer (25 mM Tris buffer, pH7.4, containing 10mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity of the cake on the glass filter was measured. Nonspecific binding was measured in the presence of 1 µM peptideYY and a 50% Inhibitory Concentration (IC50) of the test compound against specific peptideYY binding was determined [Endocrinology, 131: 2090(1992)]. The results are summarized in Table 1.

TABLE 1

Inhibitory activities on NPY receptor binding

| Compounds | IC50 (nM) |
|---|---|
| Example 1 | 4.6 |
| Example 2 | 3.0 |

As shown above, compounds of this invention potently inhibited peptideYY (NPY homologue) binding to NPY Y5 receptors.

Pharmacological Test 2 (Antagonistic Effect on bPP-induced Feeding Behavior)

A guide cannula (external diameter 0.8 mm, internal diameter 0.5 mm, length 10 mm) was inserted stereotaxicly into the right lateral ventricle of male SD rats (7-8 weeks old, 200-300 g) anesthetized with pentobarbital (single intraperitoneal administration of 50 mg/kg) and fixed by dental resin. The top of the cannula was located 0.9 mm behind bregma, 1.2 mm to the right of median line and 1.5 mm depth from the brain surface so that, when injection needle is inserted into the guide cannula, the needle extends 2 mm beyond the tip of the guide cannula and reaches the lateral ventricle. After about 1-week recovery period, bovine pancreatic polypeptide (bPP, 5 µg/10 µL/head, 0.01M, pH7.4 phosphate buffered saline solution containing 0.05% bovine serum albumin) was injected into the lateral ventricle. A test compound suspended in aqueous 0.5% methylcellulose was administered orally 2 hours before the administration of bPP and the food consumption was measured 2 hours after administration of bPP.

Compounds of this invention significantly inhibited the increase in food consumption induced by bPP (NPY homologue) which was administered to the lateral ventricle.

Compounds of the general formula (I) can be administered orally or parenterally and may be formulated in the form suitable for administration to provide an agent for treatment of various diseases related to NPY, which include, for example, cardiovascular disorders (for example hypertension, nephropathy, heart disease, vasospasm, arteriosclerosis), central nervous system disorders (for example bulimia, depression, anxiety, seizure, epilepsy, dementia, pain, alcoholism, drug withdrawal), metabolic diseases (for example obesity, diabetes, hormone abnormality, hypercholesterolemia, hyperlipidemia), sexual and reproductive dysfunction, gastro-intestinal motility disorder, respiratory disorder, inflammation or glaucoma and the like, preferably, bulimia, obesity, diabetes and the like. In clinical use, compounds of this invention can be administered after being formulated, together with pharmaceutically acceptable additives, into an appropriate preparation according to the mode of administration. For said additives, those which are usually used in the field of pharmaceutical formulation may be used, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, sodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin.

A mixture with said additives may be formulated in the form of solid preparations (for example tablets, capsules, granules, powder, suppositories); or liquid preparations (for example syrups, elixirs, injections). Such preparations may be formulated according to techniques well-known in the art of pharmaceutical formulation. Liquid preparations may be in the form of preparations which are dissolved or suspended in water or other appropriate media when used and especially injectable preparations may be dissolved or suspended in physiological saline or glucose solution if necessary, optionally together with a buffer and preservative.

Such preparations may contain 0.1 to 100 wt. %, preferably 1.0 to 60 wt. % of compounds of this invention and may also contain therapeutically effective other compounds.

The compounds of the present invention can be used in combination with other agents useful for treating metabolic and/or feeding disorders. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating metabolic and/or feeding disorders includes in principle any combination with any pharmaceutical composition useful for treating metabolic and/or feeding disorders.

One embodiment of the term "mammal" is a "human," said human being either male or female. The instant compounds are also useful for treating or preventing obesity and obesity related disorders in cats and dogs. As such, the term "mammal" includes companion animals such as cats and dogs.

The term "mammal in need thereof" refers to a mammal who is in need of treatment or prophylaxis as determined by a researcher, veterinarian, medical doctor or other clinician.

When compounds of this invention are used clinically, the dose and frequency of dosage may be varied depending upon the sex, age, body weight, the degree of symptoms and the kind and range of the desired treatment effects. A daily dose for an adult is 0.01-10 mg/kg, preferably 0.03-3 mg/kg orally, or 0.001-10 mg/kg, preferably 0.001-0.1 mg/kg parenterally, preferably in a single dose or in divided doses.

An ordinarily skilled physician, veterinarian or clinician can readily determine and prescribe the effective amount of the drug required to prevent, counter or arrest the progress of the condition.

EXAMPLES

The following examples are provided so that the present invention may be more concretely illustrated but they should not be construed as limiting the invention in any way.

Example 1

Preparation of trans-N-[1-(2-fluorophenyl)-3-pyrazolyl]-3-oxospiro[6-azaisobenzofuran-1(3H),1'-cyclohexane]-4'-carboxamide 6-oxide Method A:

mCPBA (419 mg) was added portionwise to a solution of trans-N-[1-(2-fluorophenyl)-3-pyrazolyl]-3-oxospiro[6-azaisobenzofuran-1(3H),1'-cyclohexane]-4'-carboxamide (150 mg) in $CHCl_3$ (6 mL), and the mixture was stirred for 1.5 hours at room temperature. The mixture was diluted with $CHCl_3$ and washed with sat. $NaHCO_3$ (twice) and brine. The organic layer was dried over magnesium sulfate and concentrated. The residue was purified by flash chromatography on silica gel (EtOAc/hexane 1/1, 2/1, 4/1 and EtOAc) and crystallization from EtOAc to yield 121.6 mg of the title compound. mCPBA and EtOAc means meta-chloroperoxybenzoic acid and ethyl acetate, respectively.

$^1$H NMR (300 MHz, DMSO-$d_6$): δ 1.8-2.2 (m, 8H), 2.7-2.9 (m, 1H), 6.90 (d, 1H, J=2.6 Hz), 7.3-7.5 (m, 3H), 7.7-7.8 (m, 1H), 7.85 (d, 1H, J=6.6 Hz), 8.11 (t, 1H, J=2.6 Hz), 8.37 (dd, 1H, J=1.5 Hz, J=6.6 Hz), 8.64 (d, 1H, J=1.5 Hz), 10.76 (brs, 1H)

DMSO means dimethylsulfoxide.

Method B:

A solution of dioxirane in acetone (30 ml, prepared by Murray's method from OXONE®, $NaHCO_3$, $H_2O$ and acetone, J. Org. Chem., vol.50, 2847-2853(1985)) was added to a solution of trans-N-[1-(2-fluorophenyl)-3-pyrazolyl]-3-oxospiro[6-azaisobenzofuran-1(3H),1'-cyclohexane]-4'-carboxamide (500 mg) in acetone (50 ml) at room temperature and the mixture was stirred for 0.5 hours at room temperature and refluxed for 1 hour. The mixture was cooled to room temperature and the precipitate was collected by filtration to yield 447.4 mg of the title compound.

Example 2

Preparation of trans-N-[1-(2-fluoro-4-hydroxyphenyl)-3-pyrazolyl]-3-oxospiro[6-azaisobenzofuran-1(3H),1'-cyclohexane]-4'-carboxamide (1) Preparation of 5-benzyloxy-2-nitro-fluorobenzene $K_2CO_3$ (8.97 g) and benzylbromide (4.25 mL) were added to a solution of 3-fluoro-4-nitrophenol (5.10 g) in anhydrous DMF (30 mL) at room temperature, and the mixture was stirred overnight. The mixture was diluted with EtOAc and washed with $H_2O$ and brine. The organic layer was dried over magnesium sulfate and concentrated. The residual solid was crystallized from EtOAc/hexane to yield 7.31 g of the title compound.

(2) Preparation of 4-benzyloxy-2-fluoroaniline hydrochloride

Raney Ni (1.5 g, 50 wt %) was added to a solution of 5-benzyloxy-2-nitro-fluorobenzene (7.31 g) in ethanol (150 mL) at room temperature. Hydrazine mono hydrate (4.8 mL) was added to the mixture at 40° C. and the mixture was stirred at 40° C. for 2 hours. Additional hydrazine mono hydrate (2.4 mL) was added at 40° C., and the mixture was stirred at 40° C. for 1 hour. The mixture was cooled and filtrated, and the filtrate was concentrated. The residue was taken up into EtOAc, and the mixture was washed with sat. NaHCO3 and brine. The organic layer was dried over $K_2CO_3$ and concentrated. The residue was purified by flash chromatography on silica gel (Hexane then 5%, 10%, 15% and 20% EtOAc/hexane). The purified oily material was dissolved in EtOAc (40 mL). 4N HCl-EtOAc (6 mL) was added to the solution with stirring to produce a precipitate, which was collected by filtration to yield 5.00 g of the title compound.

(3) Preparation of 4-benzyloxy-2-fluorophenylhydrazine hydrochloride

A solution of $NaNO_2$ (1.38 g) in $H_2O$ (8 mL) was added to a suspension of 4-benzyloxy-2-fluoroaniline (5.0 g) in 6N HCl (24 mL) at 0° C. After 30 minutes stirring, a solution of $SnCl_2$ (7.7 g) in 6N HCl (24 mL) was added to the mixture at 0° C. The mixture was allowed to warm to room temperature and stirred for 1.5 hours to produce a precipitate. The precipitate was collected by filtration to yield 4.15 g of the title compound.

(4) Preparation of 3-Amino-1-(4-benzyloxy-2-fluorophenyl)-pyrazoline

NaOMe (25 wt. % solution in MeOH, 7.75 mL) and acrylonitrile (2.1 mL) were added to a solution of 4-benzyloxy-2-fluorophenylhydrazine hydrochloride (4.15 g) in MeOH (40 mL) at room temperature. The mixture was stirred at room temperature for 30 minutes and refluxed overnight. Additional NaOMe (25 wt. % solution in MeOH, 3.9 mL) and acrylonitrile (1.05 ml) were added to the reaction mixture and refluxed for 7.5 hours. The mixture was diluted with EtOAc and washed with sat. $NaHCO_3$ and brine. The organic layer was dried over anhydrous $MgSO_4$ and concentrated. The residue was crystallized from $CHCl_3$/hexane to yield 3.86 g of the title compound. NaOMe and MeOH means sodium methoxide and methanol, respectively.

(5) Preparation of 3-Amino-1-(4-benzyloxy-2-fluorophenyl)-pyrazole $MnO_2$ (2.66 g) was added to a solution of 3-amino-1-(4-benzyloxy-2-fluorophenyl) pyrazoline (3.86 g) in $CH_2Cl_2$ (40 mL), and the mixture was stirred at room temperature for 4 hours. The precipitate ($MnO_2$) was filtered off, and the filtrate was concentrated. The residue was purified by flash chromatography on silica gel (EtOAc/hexane 1/9, 1/4, 1/2 and 1/1) and crystallization from EtOAc/hexane to yield 1.04 g of the title compound.

(6) Preparation of trans-N-[1-(4-benzyloxy-2-fluorophenyl)-3-pyrazolyl]-3-oxospiro[6-azaisobenzofuran-1(3H),1'-cyclohexane]-4'-carboxamide 1-[3-(Dimethylamino)propyl]-3-ethylcarbodiimide hydrochloride (400 mg) was added to a mixture of trans-3-oxospiro[6-azaisobenzofuran-1(3H),1'-cyclohexane]-4'-carboxylic acid (436 mg) and 3-amino-1-(4-benzyloxy-2-fluorophenyl)pyrazole (500 mg) in pyridine (10 mL), and the mixture was stirred overnight. The reaction mixture was poured into a mixture of H$_2$O (30 mL) and EtOAc (5 mL), and the mixture was stirred for 30 minutes. A precipitate was collected by filtration, and the filtrate was partitioned. The organic layer was washed with 10% citric. acid, sat. NaHCO$_3$ and brine, dried over MgSO$_4$ and concentrated. The residue and the above precipitate were combined and crystallized from EtOAc to yield 783.7 mg of the title compound.

(7) Preparation of trans-N-[1-(2-fluoro-4-hydroxyphenyl)-3-pyrazolyl]-3-oxospiro[6-azaisobenzofuran-1(3H),1'-cyclohexane]-4'-carboxamide 10% palladium on activated carbon (100 mg, type M, water ~50%, Pd 10%, dry weight basis) was added to a solution of trans-N-[1-(4-benzyloxy-2-fluorophenyl)-3-pyrazolyl]-3-oxospiro[6-azaisobenzofuran-1(3H),1'-cyclohexane]-4'-carboxamide (783.7 g) in THF (100 mL). The mixture was stirred under hydrogen atmosphere at room temperature for 24 hours. The catalyst was filtered off, and the filtrate was concentrated. The residue was purified by flash chromatography on silica gel (hexane, EtOAc/hexane 1/4, 1/2, 1/1, 2/1 and 4/1) and crystallization from EtOAc to yield 531.7 mg of the title compound. THF means tetrahydrofuran.

$^1$H NMR (300 MHz, DMSO-d$_6$): δ 1.8-2.2 (m, 8H), 2.7-2.9 (m, 1H), 6.6-6.8 (m, 2H), 6.81 (d, 1H, J=2.5 Hz), 7.45 (t, 1H, J=8.9 Hz), 7.87 (dd, 1H, J=1.0 Hz, J=4.9 Hz), 7.9 (t, 1H, J=2.5 Hz), 8.89 (d, 1H, J=4.9 Hz), 9.13 (d, 1H, J=1.0 Hz), 10.72 (brs, 1H)

Example 3

Preparation of cis-N-[1-(2-fluorophenyl)-3-pyrazolyl]-4'-hydroxy-3-oxospiro[6-azaisobenzofuran-1(3H),1'-cyclohexane]-4'-carboxamide (1)Preparation of cis-4'-hydroxy-3-oxospiro[6-azaisobenzofuran-1(3H), 1'-cyclohexane]-4'-carboxylic acid Trimethylsilyl cyanide (7.4 mL) was added to a mixture of spiro[6-azaisobenzofuran-1(3H),1'-cyclohexane]-3,4'-dione (5.0 g) and triethylamine (0.65 mL) in anhydrous THF (50 mL) at room temperature. The mixture was stirred at room temperature for 3 hours. Additional trimethylsilyl cyanide (2 mL) was added to the reaction mixture, and the mixture was stirred at room temperature for 2 hours. The reaction mixture was concentrated. A mixture of conc. H$_2$SO$_4$ (20 mL) and H$_2$O (80 mL) was added to the residue and the mixture was refluxed for 20 hours. After cooling, the mixture was adjusted to pH 4 by addition of 5 N sodium hydroxide with cooling by ice-bath. A precipitate produced was collected and washed with H$_2$O and EtOAc to afford 1.31 g (21.6%) of the title compound.

(2) Preparation of cis-N-[1-(2-fluorophenyl)-3-pyrazolyl]-4'-hydroxy-3-oxospiro[6-azaisobenzofuran-1(3H),1'-cyclohexane]-4'-carboxamide 1-[3-(Dimethylamino)propyl]-3-ethylcarbodiimide hydrochloride (1.0 g) was added to a mixture of cis-4'-hydroxy-3-oxospiro[6-azaisobenzofuran-1(3H),1'-cyclohexane]-4'-carboxylic acid (1.0 g) and 3-amine-1-(2-fluorophenyl)pyrazole (0.70 g) in pyridine (20 mL), and the mixture was stirred overnight. The reaction mixture was diluted with EtOAc and washed with H$_2$O, 10% citric acid, sat. NaHCO$_3$ and brine. The organic layer was dried over MgSO$_4$ and concentrated. The residue was purified by flash chromatography on silica gel (Hexane, EtOAc/hexane=1/4, CHCl$_3$, EtOAc/CHCl$_3$=1/4, 1/2, 1/1, 2/1 and 4/1) and crystallization from EtOAc to yield 557.8 mg of the title compound.

$^1$HNMR(300 MHz, DMSO-d$_6$): δ 1.85-2.05(m, 2H), 2.05-2.25 (m, 4H), 2.25-2.4 (m, 2H), 6.03 (s, 1H), 6.91 (d, 1H, J=2.5 Hz), 7.3-7.5 (m, 3H), 7.7-7.8 (m, 1H), 7.88 (dd, 1H, J=0.8 Hz, J=4.9 Hz), 8.15 (t, 1H, J=2.5 Hz), 8.90 (d, 1H, J=4.9 Hz), 9.11 (d, 1H, J=0.8 Hz), 9.98 (brs, 1H)

Example 4

Preparation of trans-N-[1-(2-fluorophenyl)-4-hydroxy-3-pyrazolyl]-3-oxospiro[6-azaisobenzofuran-1(3H),1'-cyclohexane]-4'-carboxamide (1) Preparation of Ethyl 4-chloro-2-(2-fluoro-phenylazo)-3-oxobutanoate A solution of NaNO$_2$ (0.96 g) in conc. H$_2$SO$_4$ (4 mL) was added to a solution of 2-fluoroaniline (1.52 g) in AcOH (23 mL) at 0° C., and the mixture was stirred for 1 hour at 0° C. The reaction mixture was added to a solution of ethyl 4-chloro-3-oxobutanoate (2.16 g) in a mixture of AcOH (10 mL) and H$_2$O (20 mL) at 0° C. and the reaction mixture was stirred for 15 minutes at 0° C. A solution of NaOAc (12.2 g) in H$_2$O (20 mL) was added to the reaction mixture at 0° C., and the reaction mixture was stirred for 1 hour at room temperature to produce a precipitate. The precipitate was collected by filtration and washed with H$_2$O to yield 2.75 g of the title compound. AcOH and NaOAc means acetic acid and sodium acetate, respectively.

(2) Preparation of Ethyl 1-(2-fluorophenyl)-4-hydroxypyrazole-3-carboxylate

KOAc (1.14 g) was added portionwise to a solution of ethyl 4-chloro-2-(2-fluoro-phenylazo)-3-oxobutanoate (2.75 g) in EtOH (30 mL), and the mixture was refluxed for 1 hour. After being cooled to room temperature, the mixture was diluted with EtOAc and washed with H$_2$O (twice) and brine. The organic layer was dried over anhydrous magnesium sulfate and concentrated in vacuo to yield 2.47 g of the title compound. KOAc means potassium acetate.

(3) Preparation of Ethyl 4-benzyloxy-1-(2-fluorophenyl) pyrazole-3-carboxylate

K$_2$CO$_3$ (2.00 g) and benzylchloride (1.2 mL) were added to a solution of ethyl 1-(2-fluorophenyl)-4-hydroxypyrazole-3-carboxylate (2.47 g) in anhydrous DMF (20 mL) at room temperature, and the mixture was stirred overnight. The mixture was diluted with EtOAc and washed with H$_2$O, sat. NaHCO$_3$ and brine. The organic layer was dried over anhydrous magnesium sulfate and concentrated in vacuo. The residue was purified by flash chromatography on silica gel (EtOAc/hexane 1/19, 1/9, 1/4 and 1/2) to yield 3.09 g of the title compound.

(4) Preparation of 4-benzyloxy-1-(2-fluorophenyl)pyrazole-3-carboxylic acid

5N NaOH (5 mL) was added to a solution of ethyl 4-benzyloxyl-(2-fluorophenyl)pyrazole-3-carboxylate(3.09 g) in EtOH (5 mL) at room temperature, and the mixture was stirred for 1.5 hours at room temperature. EtOH (5 mL) was added and stirred for 0.5 hours at 60° C. After cooling to room temperature, H$_2$O (5 mL) and conc. H$_2$SO$_4$ (0.7 mL) were added to the reaction mixture with stirring to produce a precipitate, and the precipitate was collected by filtration to yield 2.09 g of the title compound.

(5) Preparation of 4-benzyloxy-3-(tert-butoxycarbonyl)amino-1-(2-fluorophenyl)pyrazole Diphenylphosphoryl azide (2.16 mL) was added to a mixture of 4-benzyloxy-1-(2-fluorophenyl)pyrazole-3-carboxylic acid (2.09 g) and triethylamine (1.39 mL) in a mixture of 1,4-dioxane (25 mL) and tBuOH (25 mL). The mixture was refluxed for 1 hour and cooled to room temperature. The mixture was diluted with EtOAc and washed with $H_2O$, 10% aq. citric acid, sat. $NaHCO_3$ and brine. The organic layer was dried over anhydrous magnesium sulfate and concentrated in vacuo. The residue was purified by flash chromatography on silica gel (EtOAc/hexane 1/19, 1/9, 1/4 and 1/2) to yield 1.30 g of the title compound.

(6) Preparation of 3-amino-4-benzyloxy-1-(2-fluorophenyl)pyrazole

TFA (2 mL) was added to a solution of 4-benzyloxy-3-(tert-butoxycarbonyl)amino-1-(2-fluorophenyl)pyrazole (1.30 g) in $CHCl_3$ (5 mL) at room temperature and the mixture was stirred for 1.5 hours at room temperature. After being neutralized with 5N NaOH, the mixture was diluted with EtOAc and washed with $H_2O$, sat. $NaHCO_3$ and brine. The organic layer was dried over anhydrous magnesium sulfate and concentrated in vacuo. The semicrystalline residue was triturated with hexane overnight and filtered to yield 742.6 mg of the title compound.

(7) Preparation of trans-N-[4-benzyloxy-1-(2-fluorophenyl)-3-pyrazolyl]-3-oxospiro[6-azaisobenzofuran-1(3H),1'-cyclohexane]-4'-carboxamide 1-[3-(Dimethylamino)propyl]-3-ethylcarbodiimide hydrochloride (100 mg) was added to a mixture of trans-3-oxospiro[6-azaisobenzofuran-1(3H),1'-cyclohexane]-4'-carboxylic acid (100 mg) and 3-amino-4-benzyloxy-1-(2-fluorophenyl)pyrazole (115 mg) in pyridine (2 mL), and the mixture was stirred for 4 hours. The reaction mixture was diluted with EtOAc and washed with $H_2O$, 10% aq. citric acid, sat. $NaHCO_3$ and brine. The organic layer was dried over anhydrous magnesium sulfate and concentrated in vacuo to yield 219 mg of a crude product of the title compound.

(8) Preparation of trans-N-[1-(2-fluorophenyl)-4-hydroxy-3-pyrazolyl]-3-oxospiro[6-azaisobenzofuran-1(3H),1'-cyclohexane]-4'-carboxamide 10% palladium on activated carbon (35 mg) was added to a solution of trans-N-[4-benzyloxy-1-(2-fluorophenyl)-3-pyrazolyl]-3-oxospiro[6-azaisobenzofuran-1(3H),1'-cyclohexane]-4'-carboxamide (219 mg) in THF (20 mL). The mixture was stirred in a hydrogen atmosphere at room temperature for 24 hours. The catalyst was filtered off, and the filtrate was concentrated in vacuo. The residue was purified by flash chromatography on silica gel (hexane, EtOAc/hexane 1/9, 1/4, 1/3 and 1/2) and crystallization from EtOAc to yield 123.2 mg of the title compound.

$^1$H NMR (300 MHz, DMSO-$d_6$): δ 1.85-2.23 (m, 8H), 2.85-2.95 (m, 1H), 7.27-7.46 (m, 3H), 7.65-7.74 (m, 1H), 7.75 (d, 1H, J=2.7 Hz), 7.87 (d, 1H, J=5.0 Hz), 8.89 (d, 1H, J=1.0 Hz, J=5.0 Hz), 9.13 (s, 1H), 9.28 (brs, 1H), 10.94 (brs, 1H)

Formulation Example 1

20.0 grams of compound of Example 1, 417 grams of lactose, 80 grams of crystalline cellulose and 80 grams of partial α-starch were blended with a V-cone blender. To the mixture was added 3.0 grams of magnesium stearate and the whole was blended. The blended powder was compressed into 3000 tablets by conventional procedure so that each tablet has a weight of 150 mg and 7.0 mm in diameter.

| The content of one tablet with a weight of 150 mg | |
|---|---|
| the compound of Example 1 | 5.0 mg |
| lactose | 104.25 mg |
| crystalline cellulose | 20.0 mg |
| partial α-starch | 20.0 mg |
| magnesium stearate | 0.75 mg |

Formulation Example 2

10.8 grams of hydroxypropylcellulose 2910 and 2.1 grams of polyethylene glycol 6000 were dissolved in 172.5 grams of purified water. To the solution was dispersed 2.1 grams of titanium oxide to provide a coating liquid. 2500 tablets prepared in Formulation example 1, was subjected to spray-coating with the coating liquid using HICOATER-MINI to provide a film coated tablet with a weight of 155 mg.

| The content of one tablet (155 mg) | |
|---|---|
| the tablet prepared in the Formulation example 1 | 150 mg |
| hydroxypropylcellulose 2910 | 3.6 mg |
| Polyethylene glycol 6000 | 0.7 mg |
| titanium dioxide | 0.7 mg |

INDUSTRIAL APPLICABILITY

Compounds of the present invention exhibit NPY antagonistic activities and are useful as agents for the treatment of various diseases related to NPY, for example, cardiovascular disorders such as hypertension, nephropathy, heart disease, vasospasm, arteriosclerosis and the like, central nervous system disorders such as bulimia, depression, anxiety, seizure, epilepsy, dementia, pain, alcoholism, drug withdrawal and the like, metabolic diseases such as obesity, diabetes, hormone abnormality, hypercholesterolemia, hyperlipidemia and the like, sexual and reproductive dysfunction, gastro-intestinal disorder, respiratory disorder, inflammation or glaucoma, and the like.

The invention claimed is:
1. A compound represented by the general formula (I-b):

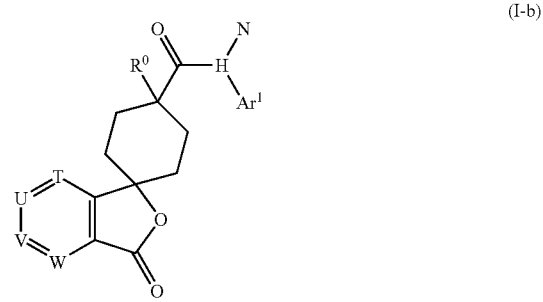

wherein $Ar^1$ represents phenyl, pyrrolyl, imidazolyl, pyrazolyl, thiazolyl, oxazolyl, isoxyazolyl, 1,2,3-triazolyl, 1,2,4-thiadiazolyl, pyridyl, pyrazinyl, pyrimidinyl, 1,2, 4-triazinyl, benzoxazolyl, benzothiazolyl, quinolyl or pyrido [3,2-b]pyridyl which may be substituted, the substituent being selected from the group consisting of hydroxy, halogen, nitro, lower alkyl, halo(lower)alkyl, hydroxy(lower)alkyl, cyclo(lower)alkyl, lower alkenyl, lower alkoxy, halo(lower) alkoxy, lower alkylthio, carboxyl, lower alkanoyl, lower alkoxycarbonyl, lower alkylene optionally substituted with oxo, and a group represented by the formula -Q-$Ar^2$;

$Ar^2$ represents an aryl or heteroaryl which may be substituted, the substituent being selected from the group consisting of halogen, cyano, lower alkyl, halo(lower) alkyl, hydroxy(lower)alkyl, hydroxy, lower alkoxy, halo(lower)alkoxy, lower alkylamino, di-lower alkylamino, lower alkanoyl and aryl;

Q represents a single bond or carbonyl;

$R^0$ represents hydrogen or hydroxy;

T, U, V and W each independently represent a nitrogen atom or a methine group which may have a substituent selected from the group consisting of halogen, lower alkyl, hydroxy and lower alkoxy, wherein at least two of which represent said methine group or a salt, ester of a carboxyl group or N-oxide derivative thereof, with the proviso that if the compound is not an N-oxide derivative, $Ar^1$ is a hydroxy substituted phenyl pyrrolyl, imidazolyl, pyrazolyl, thiazolyl, oxazolyl, isoxyazolyl, 1, 2, 3-triazolyl, 1,2,4-thiadiazolyl, pyridyl, pyrazinyl, pyrimidinyl, 1,2,4-triazinyl, benzoxazolyl, benzothiazolyl, quinolyl or pyrido[3,2-b]pyridyl group, or alternatively $R^0$ is hydroxy.

2. The compound of claim 1, wherein $Ar^1$ is a hydroxy substituted phenyl, pyrrolyl, imidazolyl, pyrazolyl, thiazolyl, oxazolyl, isoxyazolyl, 1,2,3-triazolyl, 1,2,4-thiadiazolyl, pyridyl, pyrazinyl, pyrimidinyl, 1, 2, 4-triazinyl, benzoxazolyl, benzothiazolyl, quinolyl or pyrido[3,2-b]pyridyl group.

3. The compound of claim 1, wherein one of T, U, V and W is nitrogen.

4. The compound of claim 1, which is a N-oxide derivative.

5. The compound of claim 1, wherein V is nitrogen and each of T, U and W is an unsubstituted methine group.

6. The compound of claim 1, which is trans-N-[1-(4-fluorophenyl)-4-hydroxy-3-pyrazolyl]-3-oxospiro[7-azaisobenzofuran-1(3H),1'-cyclohexane]-4'-carboxamide, trans-3-oxo-N-(4-hydroxy-1-phenyl-3-pyrazolyl)spiro[4-azaisobenzofuran-1(3H),1'-cyclohexane]-4'-carboxamide, trans-3-oxo-N-(4-hydroxy-1-phenyl-3-pyrazolyl)spiro[6-azaisobenzofuran-1(3H),1'-cyclohexane]-4'-carboxamide, trans-N-[1-(4-fluorophenyl)-4-hydroxy-3-pyrazolyl]-3-oxospiro[6-azaisobenzofuran-1(3H),1'-cyclohexane]-4'-carboxamide or trans-N-[1-(2-fluorophenyl)-4-hydroxy-3-pyrazolyl]-3-oxospiro[6-azaisobenzofuran-1(3H),1'-cyclohexane]-4'-carboxamide.

7. The compound of claim 1, which is cis-N-[1-(2-fluoro-4-hydroxyphenyl)-3-pyrazolyl]-4'-hydroxy-3-oxospiro[6-azaisobenzofuran-1(3H),1'-cyclohexane]-4'-carboxamide.

8. The compound of claim 1, which is trans-N-[1-(4-fluorophenyl)-4-hydroxy-3-pyrazolyl]-3-oxospiro[7-azaisobenzofuran-1(3H),1'-cyclohexane]-4'-carboxamide.

9. The compound of claim 1, which is trans-3-oxo-N-(4-hydroxy-1-phenyl-3-pyrazolyl)spiro[4-azaisobenzofuran-1(3H),1'-cyclohexane]-4'-carboxamide.

10. The compound of claim 1, which is trans-3-oxo-N-(4-hydroxy-1-phenyl-3-pyrazolyl)spiro[6-azaisobenzofuran-1(3H),1'-cyclohexane]-4'-carboxamide.

11. The compound of claim 1, which is trans-N-[1-(4-fluorophenyl)-4-hydroxy-3-pyrazolyl]-3-oxospiro[6-azaisobenzofuran-1(3H),1'-cyclohexane]-4'-carboxamide.

12. The compound of claim 1, which is trans-N-[1-(2-fluorophenyl)-4-hydroxy-3-pyrazolyl]-3-oxospiro[6-azaisobenzofuran-1(3H),1'-cyclohexane]-4'-carboxamide.

13. A method for the treatment of obesity which comprises administering to a mammal in need thereof a therapeutically effective amount of a compound of claim 1.

14. A pharmaceutical composition which comprises a pharmaceutically effective amount of a compound of claim 1 together with a pharmaceutically acceptable additive.

* * * * *